US009042990B2

(12) United States Patent
Carlson et al.

(10) Patent No.: US 9,042,990 B2
(45) Date of Patent: *May 26, 2015

(54) STIMULATION ELECTRODE SELECTION

(71) Applicant: Medtronic, Inc., Minneapolis, MN (US)

(72) Inventors: David L. Carlson, Fridley, MN (US); Randy M. Jensen, Hampton, MN (US); Timothy J. Denison, Minneapolis, MN (US); Jianping Wu, Shoreview, MN (US); Gabriela C. Molnar, Fridley, MN (US); Scott R. Stanslaski, Shoreview, MN (US); William J. Marks, Jr., San Francisco, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/161,389

(22) Filed: Jan. 22, 2014

(65) Prior Publication Data

US 2014/0135870 A1 May 15, 2014

Related U.S. Application Data

(60) Continuation of application No. 13/827,537, filed on Mar. 14, 2013, now Pat. No. 8,670,830, which is a division of application No. 12/563,845, filed on Sep. 21, 2009, now Pat. No. 8,428,733.

(60) Provisional application No. 61/105,943, filed on Oct. 16, 2008.

(51) Int. Cl.
*A61N 1/36* (2006.01)
*A61N 1/05* (2006.01)
*A61N 1/372* (2006.01)

(52) U.S. Cl.
CPC .......... *A61N 1/36067* (2013.01); *A61N 1/0529* (2013.01); *A61N 1/0534* (2013.01); *A61N 1/36082* (2013.01); *A61N 1/36185* (2013.01); *A61N 1/37247* (2013.01)

(58) Field of Classification Search
USPC .......................................... 607/45
See application file for complete search history.

(56) References Cited

U.S. PATENT DOCUMENTS 6,066,163 A 5/2000 John
7,305,268 B2 * 12/2007 Gliner et al. .................... 607/45

(Continued)

OTHER PUBLICATIONS

Chen et al, "Intra-operative recordings of local field potentials can help localize the subthalamic nucleus in Parkinson's disease surgery," Exp Neural. Mar. 2006, 198(1):214-21, Epub Jan. 5, 2006.

(Continued)

*Primary Examiner* — Paula J Stice
(74) *Attorney, Agent, or Firm* — Shumaker & Sieffert, P.A.

(57) ABSTRACT

Bioelectrical signals may be sensed within a brain of a patient with a plurality of sense electrode combinations. A stimulation electrode combination for delivering stimulation to the patient to manage a patient condition may be selected based on the frequency band characteristics of the sensed signals. In some examples, a stimulation electrode combination associated with the sense electrode combination that sensed a bioelectrical brain signal having a relatively highest relative beta band power level may be selected to deliver stimulation therapy to the patient. Other frequency bands characteristics may also be used to select the stimulation electrode combination.

41 Claims, 10 Drawing Sheets

(56) References Cited

U.S. PATENT DOCUMENTS

| | | | |
|---|---|---|---|
| 7,519,431 | B2 | 4/2009 | Goetz et al. |
| 8,121,694 | B2 | 2/2012 | Molnar et al. |
| 8,428,733 | B2 | 4/2013 | Carlson et al. |
| 8,532,757 | B2 | 9/2013 | Molnar et al. |
| 8,538,513 | B2 | 9/2013 | Molnar et al. |
| 2006/0217781 | A1 | 9/2006 | John |
| 2007/0032834 | A1 | 2/2007 | Gliner et al. |
| 2007/0203545 | A1 | 8/2007 | Stone et al. |
| 2007/0225674 | A1 | 9/2007 | Molnar et al. |
| 2009/0082691 | A1 | 3/2009 | Denison et al. |
| 2009/0192556 | A1 | 7/2009 | Wu et al. |
| 2011/0144521 | A1 | 6/2011 | Molnar et al. |
| 2011/0144715 | A1 | 6/2011 | Molnar et al. |
| 2013/0197605 | A1 | 8/2013 | Carlson et al. |

OTHER PUBLICATIONS

Wingeier et al., "Intra-operative STN DBS attenuates the prominent beta rhythm in the STN in Parkinson's disease," Exp Neural. Jan. 2006; 197(1):244-51. Epub Nov. 10, 2005.

Kuhn et al, "High-frequency stimulation of the subthalamic nucleus suppresses oscillatory beta activity in patients with Parkinson's disease in parallel with improvement in motor performance," J Neurosci. Jun. 11, 2008; 28(24):6165-73.

Marceglia et al, "Basal ganglia local field potentials: applications in the development of new deep brain stimulation devices for movement disorders," Expert Rev Med Devices. Sep. 2007; 4(5):605-14.

Jensen et al., "Information, Energy, and Entropy: Design Principles for Adaptive, Therapeutic Modulation of Neural Circuits," IEEE conference, Edinburgh, Sep. 15-19, 2008, pp. 32-39.

Debatisse et al., "DBS in STN and macrorecording using electrodes of stimulation: what can be done and where we are?" 14th Meeting of the World Society for Stereotactic and Functional Neurosurgery, Rome, Jun. 13-17, 2005, 1 p.

International Search Report for International Application No. PCT/US2009/057862, dated Apr. 21, 2010, 6 pp.

Chen et al., "Deep brain stimulation of the subthalamic nucleus: A two-edged sword," Current Biology vol. 16, No. 2, Nov. 21, 2006, pp. R952-R953.

Ince, et al., "Selection of Optimal Programming Contacts Based on Local Field Potential Recordings from Subthalamic Nucleus in Patients With Parkinson's Disease," Neurosurgery, vol. 67, No. 2, Aug. 2010, pp. 390-397.

Yoshida et al., "Value of subthalamic nucleus local field potentials recordings in predicting stimulation parameters for deep brain stimulation in Parkinson's disease," J Neurol Neurosurg Psychiatry, 2010, 5 pp.

Chen, et al., "Intra-operative recordings of local field potentials can help localize the subthalamic nucleus in Parkinson's disease surgery," Exp Neural. Mar. 2006, 198(1):214-21, Epub Jan. 5, 2006.

Prosecution History from U.S. Appl. No. 12/563,845 filed Sep. 21, 2009, from Oct. 11, 2012 through Dec. 24, 2012, 18 pp.

Prosecution History from U.S. Appl. No. 13/827,537 filed Mar. 14, 2013, from Oct. 10, 2013 through Jan. 10, 2014, 19 pp.

Prosecution History from U.S. Appl. No. 12/639,717 filed Dec. 16, 2009, from May 21, 2012 through Jul. 18, 2013, 116 pp.

Prosecution History from U.S. Appl. No. 12/639,678 filed Dec. 16, 2009, from May 21, 2012 through Aug. 19, 2013, 121 pp.

U.S. Appl. No. 14/161,363, filed Jan. 22, 2014, by Carlson et al.

Response to Office Action dated May 23, 2014, from U.S. Appl. No. 14/161,363, filed Aug. 25, 2014, 16 pp.

Office Action from U.S. Appl. No. 14/161,363, dated May 23, 2014, 14 pp.

Final Office Action from U.S. Appl. No. 14/161,363, dated Oct. 27, 2014, 11 pp.

Response to Final Office Action dated Oct. 27, 2014, from U.S. Appl. No. 14/161,363, dated Jan. 5, 2015, 13 pp.

Notice of Allowance from U.S. Appl. No. 14/161,363, dated Jan. 20, 2015, 9 pp.

\* cited by examiner

| SENSE ELECTRODE COMBINATION | β POWER 1 | β POWER 2 | RELATIVE POWER | OVERALL SCORE | CONFIDENCE SCORE |
|---|---|---|---|---|---|
| COMBINATION 1 | 322 | 34 | 54 | 98 | 87% |
| COMBINATION 2 | 267 | 35 | 49 | 92 | 79% |
| COMBINATION 3 | 34 | 5 | 12 | 18 | 75% |

FIG. 9

STIMULATION ELECTRODE SELECTION

This application is a continuation of U.S. patent application Ser. No. 13/827,537, which was filed on Mar. 14, 2013 and is entitled, "STIMULATION ELECTRODE SELECTION." U.S. patent application Ser. No. 13/827,537 issued as U.S. Pat. No. 8,670,830 on Mar. 12, 2014. U.S. patent application Ser. No. 13/827,537 is a divisional of U.S. patent application Ser. No. 12/563,845, which was filed on Sep. 21, 2009, and is entitled, "STIMULATION ELECTRODE SELECTION," and issued as U.S. Pat. No. 8,428,733 on Apr. 23, 2013. U.S. patent application Ser. No. 12/563,845 claims the benefit of U.S. Provisional Patent Application No. 61/105,943, which was filed on Oct. 16, 2008 and is entitled, "STIMULATION ELECTRODE SELECTION." The entire content of U.S. patent application Ser. Nos. 13/827,537, 12/563,845, and 61/105,943 is incorporated herein by reference.

TECHNICAL FIELD

The disclosure relates to medical devices, and, more particularly, to configuration of therapy parameters for a medical device.

BACKGROUND

Patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Movement disorders may be found in patients with Parkinson's disease, multiple sclerosis, and cerebral palsy, among other conditions. Delivery of electrical stimulation and/or a fluid (e.g., a pharmaceutical drug) by a medical device to one or more sites in a patient, such as a brain, spinal cord, leg muscle or arm muscle, in a patient may help alleviate, and in some cases, eliminate symptoms associated with movement disorders.

During a programming session, which may occur during implant of the medical device, during a trial session, or during a follow-up session after the medical device is implanted in the patient, a clinician may generate one or more therapy programs that provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. Where electrical stimulation is delivered in the form of electrical pulses, for example, the parameters may include an electrode combination, an amplitude, which may be a current or voltage amplitude, a pulse width, and a pulse rate for the pulses.

SUMMARY

In general, the disclosure is directed toward selecting one or more electrodes from an array of electrodes to deliver electrical stimulation to a brain of a patient to provide therapy to manage a patient condition, such as a movement disorder. The one or more selected electrodes used to deliver stimulation may be referred to as a stimulation electrode combination, and may include one electrode (e.g., unipolar stimulation between the electrode and the can) or two or more electrodes (e.g., bipolar stimulation). In examples described herein, the stimulation electrode combination may be selected based on bioelectrical signals sensed within the patient's brain. In particular, bioelectrical signals may be sensed within the brain with a plurality of sense electrode combinations, and the stimulation electrode combination may be selected based on frequency domain characteristics of the sensed signals. For example, the stimulation electrode combination may be selected based on the sense electrode combination that is associated with the sensed bioelectrical signal having the greatest beta band power (or energy) to signal power ratio. Other frequency domain characteristics and the power levels in other frequency bands may also be used to select the stimulation electrode combination. In addition, in some examples, a stimulation electrode combination may be selected based on an impedance of an electrical path including the stimulation electrodes.

In one aspect, the disclosure is directed to a method comprising sensing a first bioelectrical signal in a brain of a patient with a first sense electrode combination, sensing a second bioelectrical signal in the brain with a second sense electrode combination that is different than the first sense electrode combination, determining a frequency domain characteristic of each of the first and second bioelectrical signals, selecting at least one of the first or second sense electrode combinations based on the frequency domain characteristics of the first and second bioelectrical signals, and selecting a stimulation electrode combination for delivering electrical stimulation to the brain of the patient based on the selected at least one of the first or second sense electrode combinations In another aspect, the disclosure is directed to a system comprising a plurality of electrodes, a sensing module that senses a first bioelectrical signal in a brain of a patient with a first sense electrode combination comprising a first subset of electrodes of the plurality of electrodes and senses a second bioelectrical signal in the brain with a second sense electrode combination that comprises a second subset of electrodes of the plurality of electrodes different than the first subset of electrodes, and a processor. The processor determines a frequency domain characteristic of each of the first and second bioelectrical signals, selects at least one of the first or second sense electrode combinations based on the frequency domain characteristics of the first and second bioelectrical signals, and selects a stimulation electrode combination for delivering electrical stimulation to the brain of the patient based on the selected at least one of the first or second sense electrode combinations.

In another aspect, the disclosure is directed to a system comprising means for sensing a first bioelectrical signal in a brain of a patient with a first sense electrode combination, means for sensing a second bioelectrical signal in the brain with a second sense electrode combination that is different than the first sense electrode combination, means for determining a frequency domain characteristic of each of the first and second bioelectrical signals, means for selecting at least one of the first or second sense electrode combinations based on the frequency domain characteristics of the first and second bioelectrical signals, and means for selecting a stimulation electrode combination for delivering electrical stimulation to the brain of the patient based on the selected at least one of the first or second sense electrode combinations.

In another aspect, the disclosure is directed to a method comprising controlling a stimulation module to deliver stimulation to a brain of a patient with a first stimulation electrode combination, sensing a first bioelectrical signal in the brain of the patient with a first sense electrode combination that is associated with the first stimulation electrode combination, determining a first frequency domain characteristic of the first bioelectrical signal, sensing a second bioelectrical signal in the brain of the patient with a second sense electrode combination that is associated with a second stimulation electrode combination, determining a second frequency domain characteristic of the second bioelectrical signal, comparing the first and second frequency domain characteristics, and controlling the stimulation module to deliver stimulation to the brain of the patient with the second stimulation electrode combination based on the comparison.

In another aspect, the disclosure is directed to a system comprising a stimulation generator that delivers stimulation to a brain of a patient with a first stimulation electrode combination, a sensing module that senses a first bioelectrical signal in the brain of the patient with a first sense electrode combination that is associated with the first stimulation electrode combination and senses a second bioelectrical signal in the brain of the patient with a second sense electrode combination that is associated with a second stimulation electrode combination, and a processor. The processor determines a first frequency domain characteristic of the first bioelectrical signal and a second frequency domain characteristic of the second bioelectrical signal, compares the first and second frequency domain characteristics, and controls the stimulation module to deliver stimulation to the brain of the patient with the second stimulation electrode combination based on the comparison.

In another aspect, the disclosure is directed to a system comprising means for controlling a stimulation module to deliver stimulation to a brain of a patient with a first stimulation electrode combination, means for sensing a first bioelectrical signal in the brain of the patient with a first sense electrode combination that is associated with the first stimulation electrode combination, means for determining a first frequency domain characteristic of the first bioelectrical signal, means for sensing a second bioelectrical signal in the brain of the patient with a second sense electrode combination that is associated with a second stimulation electrode combination, means for determining a second frequency domain characteristic of the second bioelectrical signal, means for comparing the first and second frequency domain characteristics, and means for controlling the stimulation module to deliver stimulation to the brain of the patient with the second stimulation electrode combination based on the comparison.

In another aspect, the disclosure is directed to a computer-readable medium comprising instructions. The instructions cause a programmable processor to perform any part of the techniques described herein.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 9 illustrates an example table that associates various sense electrode combinations with beta band power levels of bioelectrical signals sensed within a brain of a patient.

DETAILED DESCRIPTION

Figure 1:
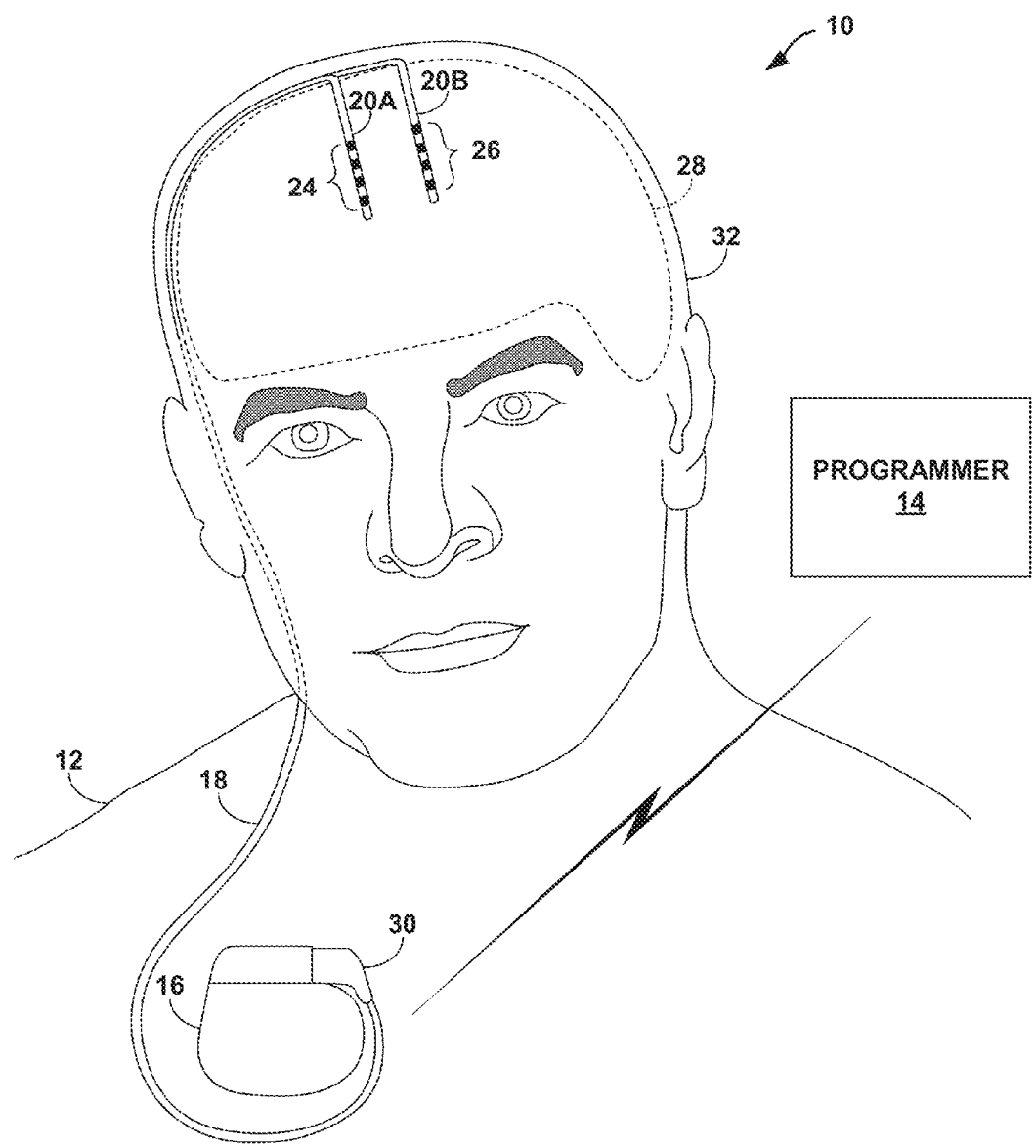
FIG. 1 is a conceptual diagram illustrating an example deep brain stimulation (DBS) system.

FIG. 1 is a conceptual diagram illustrating an example therapy system 10 that delivers therapy to control a patient condition, such as a movement disorder or a neurodegenerative impairment of patient 12. Patient 12 ordinarily will be a human patient. In some cases, however, therapy system 10 may be applied to other mammalian or non-mammalian non-human patients. While movement disorders and neurodegenerative impairment are primarily referred to herein, in other examples, therapy system 10 may provide therapy to manage symptoms of other patient conditions, such as, but not limited to, seizure disorders or psychological disorders.

A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions. Although movement disorders are primarily referred to throughout the remainder of the application, the therapy systems and methods described herein are also useful for controlling symptoms of other conditions, such as neurodegenerative impairment.

Therapy system 10 includes medical device programmer 14, implantable medical device (IMD) 16, lead extension 18, and leads 20A and 20B with respective sets of electrodes 24, 26. In the example shown in FIG. 1, electrodes 24, 26 of leads 20A, 20B are positioned to deliver electrical stimulation to a tissue site within brain 28, such as a deep brain site under the dura mater of brain 28 of patient 12. In some examples, delivery of stimulation to one or more regions of brain 28, such as the subthalamic nucleus, globus pallidus or thalamus, may be an effective treatment to manage movement disorders, such as Parkinson's disease.

IMD 16 includes a therapy module that includes a stimulation generator that generates and delivers electrical stimulation therapy to patient 12 via a subset of electrodes 24, 26 of leads 20A and 20B, respectively. The subset of electrodes 24, 26 that are used to deliver electrical stimulation to patient 12, and, in some cases, the polarity of the subset of electrodes 24, 26, may be referred to as a stimulation electrode combination. As described in further detail below, the stimulation electrode combination may be selected based on one or more frequency domain characteristics of a bioelectrical brain signal that is sensed by a sense electrode combination that is associated with the stimulation electrode combination. In some examples, the bioelectrical signals sensed within brain 28 may reflect changes in electrical current produced by the sum of electrical potential differences across brain tissue. Examples of bioelectrical brain signals include, but are not limited to, electrical signals generated from local field potentials within one or more regions of brain 28, an electroencephalogram (EEG) signal or an electrocorticogram (ECoG) signal.

In some examples, the bioelectrical brain signals that are used to select a stimulation electrode combination may be sensed within the same tissue site of brain 28 as the target tissue site for the electrical stimulation. As previously indicated, these tissue sites may include tissue sites within the thalamus, subthalamic nucleus or globus pallidus of brain 28. Thus, in some examples, both a stimulation electrode combination and a sense electrode combination used to sense bioelectrical brain signals may be selected from the same set of electrodes 24, 26.

In some examples, the stimulation electrode combination may be selected during a programming session following the implantation of IMD 16 and leads 20A, 20B in patient 12. For example, during the programming session, bioelectrical brain signals may be sensed within brain 28 via each of at least two different sense electrode combinations. Each sense electrode combination may include a different subset of two or more electrodes 24, 26. Frequency domain characteristics of each of the sensed bioelectrical brain signals may be compared to each other and a sense electrode combination may be selected based on the comparison. An example of a frequency domain characteristic may include power level (or energy level) within a particular frequency band. The power level may be determined based on, for example, a spectral analysis of a bioelectrical brain signal. The spectral analysis may indicate the distribution over frequency of the power contained in a signal, based on a finite set of data.

In some examples, the sense electrode combination that sensed the bioelectrical brain signal having the highest relative beta band power (or energy) may be selected. The relative beta band power may be a ratio of the power in a beta band of the sensed signal to the overall power of the sensed signal. The selected sense electrode combination may be associated with a stimulation electrode combination, which may be programmed into IMD 16 in order to deliver stimulation therapy to brain 28. In this way, the stimulation electrode combination may be selected based on a frequency domain characteristic of a bioelectrical brain signal.

In some examples, other stimulation parameter values may be selected based on the frequency domain characteristics of a bioelectrical brain signal sensed via a sense electrode combination associated with a stimulation electrode combination. For example, a beta band power level may be associated with a stimulation amplitude value that may provide efficacious therapy to patient 12.

One or more specific frequency bands may be more revealing of a useful target tissue site for providing stimulation therapy to patient 12 than other frequency bands. Processor 40 (FIG. 3) may perform a spectral analysis of the bioelectrical brain signal in the revealing frequency bands. The spectral analysis of a biosignal may indicate the power level of each bioelectrical signal within each given frequency band over a range of frequencies. While the beta frequency band is primarily referred to herein, in other examples, processor 40 may select a stimulation electrode combination based on the power level within one or more frequency bands other than the beta band. The beta band may include a frequency range of about 10 Hertz (Hz) to about 35 Hz, such as about 10 Hz to about 30 Hz or 13 Hz to about 30 Hz.

Figure 2:
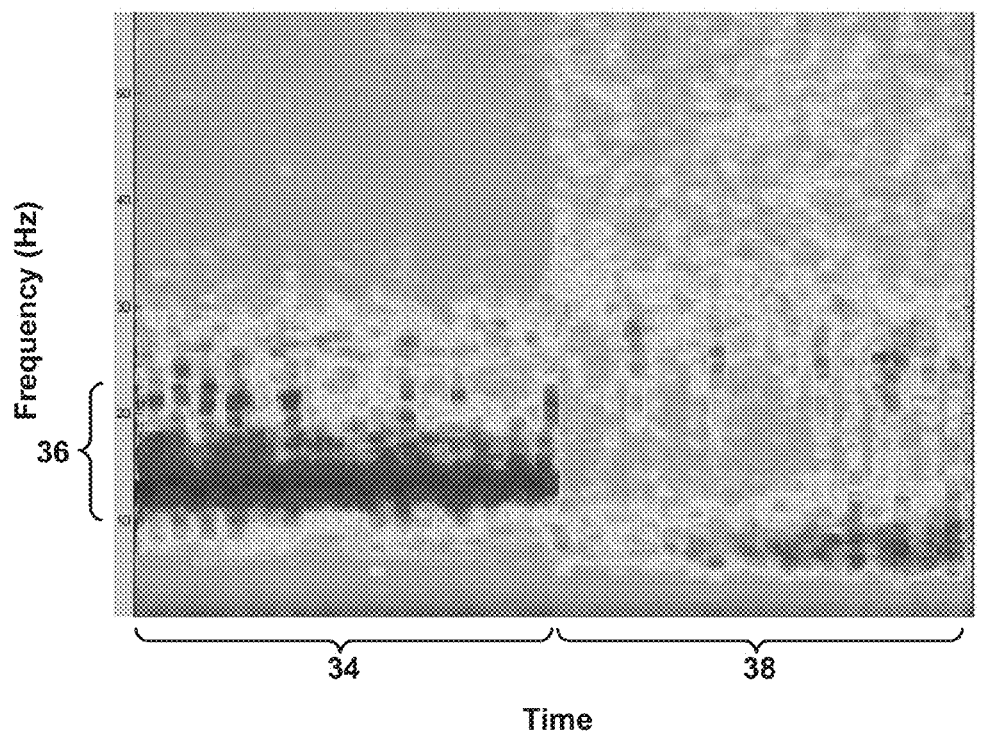
FIG. 2 is an example spectrogram of a bioelectrical brain signal sensed within a brain of a patient.

Some movement disorder symptoms of patient 12, such as bradykinesia, may be associated with abnormal synchronization of beta frequency band activity within particular structures of brain 28 of patient 12. For example, FIG. 2 is an example spectrogram of bioelectrical brain signals sensed within a subthalamic nucleus of a brain of a human subject. The y-axis of the spectrogram indicates the frequency band of the bioelectrical brain signal, the x-axis indicates time, and the z-axis, which extends substantially perpendicular to the plane of the image of FIG. 2, as indicated by the color of the spectrogram, indicates a power level of the bioelectrical brain signal. The spectrogram provides a three-dimensional plot of the energy of the frequency content of a bioelectrical brain signal as it changes over time.

In a first time period 34, the human subject is in a pathological state and is not under the influence of therapy to mitigate effects of a movement disorder. As shown in FIG. 2, in the first time period 34, a power level of the bioelectrical brain signal of the human subject in a subset of the beta band 36 is relatively high, as indicated by the relatively intense color in FIG. 2. The subset of the beta band 36 in the example shown in FIG. 2 includes a frequency range of about 10 Hz to about 20 Hz. In a second time period 38, the human subject is under the influence of pharmaceutical agents to mitigate effects of the movement disorder. As shown in FIG. 2, compared to the first time period 34, the beta band activity decreases during the second time period 38 in which the human subject is receiving movement disorder therapy.

The spectrogram shown in FIG. 2 demonstrates that a power level in a beta band of a bioelectrical brain signal may be relatively high in patients suffering from movement disorder symptoms, and the power level may decrease upon the receipt of therapy to manage the movement disorder symptoms. Thus, a high beta band power level may be a marker for a movement disorder.

In some patients, identifying the location within brain 28 that demonstrates the highest relative beta band activity may indicate the location at which electrical stimulation may relatively effectively suppress the abnormal synchronization of beta frequency band activity associated with the patient's movement disorder. The location within brain 28 that demonstrates the highest relative beta band activity may indicate the location within brain 28 that is a suitable stimulation target for electrical stimulation to manage the patient's movement disorder. As a result of directing stimulation to this stimulation target that exhibits a relatively high level of beta band energy, the intensity of stimulation that IMD 16 may deliver in order to provide efficacious stimulation therapy may be lower than the intensity of stimulation that may be required to provide efficacious stimulation therapy to other tissue sites that may be further from the stimulation target or less functionally related to the stimulation target. An intensity of stimulation may be related to the current or voltage amplitude of a stimulation signal, a frequency of the stimulation signal, and, if the signal comprises a pulse, a pulse width or pulse shape of the stimulation signal.

In some examples, the sense electrode combination that senses the highest relative beta band activity within brain 28 may provide the best relative efficacy when stimulation therapy is delivered via the subset of electrodes of the sense electrode combination. Thus, in some examples, the stimulation electrode combination may comprise the subset of electrodes of the sense electrode combination. In some examples, electrical stimulation may be delivered to substantially the same location at which a bioelectrical brain signal having a relatively high relative beta band power was sensed in order to effectively suppress the abnormal synchronization of beta frequency band activity associated with the patient's movement disorder.

In other examples, the stimulation electrode combination may comprise a different subset of electrodes than the sense electrode combination. For example, a sense electrode combination may include at least two electrodes 24, 26 of leads 20A, 20B, whereas a stimulation electrode combination may include a single electrode of leads 20A, 20B (e.g., to provide unipolar stimulation) or more than two electrodes. In a unipolar configuration, stimulation may be provided between an electrode of one of the leads 20A, 20B and a housing of IMD 16 or another reference. In the case of stimulation electrode combinations, it may be possible for more than one electrode to share a polarity. Sensing in a unipolar configuration may not be useful for identifying useful bioelectrical brain signals because sensing between an electrode of one of the leads 20A, 20B and a housing of IMD 16 or another reference may result in the sensing of cardiac activity of patient 12, which may dominate and mask the brain activity.

If the stimulation electrode combination and an associated sense electrode combination include at least one different electrode, the stimulation electrode combination and sense electrode combination may be positioned within different parts of brain 28. The parts may or may not overlap.

In some examples, the sense electrode combination that senses the highest relative beta band activity within brain 28 may be mapped to a stimulation electrode combination that may provide relatively efficacious stimulation therapy. For example, the subset of electrodes of the sense electrode combination and the subset of electrodes of the stimulation electrode combination may be related by a functional relationship between different regions of brain 28. For example, a sense electrode combination that senses a bioelectrical signal having a relatively high beta band power within a first part of the thalamus may be mapped to a second part of the thalamus that is functionally connected to first part. This functional relationship may indicate that if electrical stimulation is delivered to the second part of the thalamus via a particular stimulation electrode combination, any irregular oscillations or other irregular brain activity within the first part of the thalamus may be effectively suppressed.

Selecting one or more stimulation electrode combinations for therapy system 10 based on sensed bioelectrical brain signals may be useful for minimizing the amount of time required to select efficacious stimulation electrode combinations. In the example shown in FIG. 1, therapy system 10 comprises eight electrodes 24, 26, whereby any combination of the eight electrodes 24, 26 may be selected to provide stimulation therapy to brain 28. In existing techniques, a clinician may randomly select and test stimulation electrode combinations in order to find an efficacious stimulation electrode combination. In some cases, the clinician's knowledge and experience selecting stimulation electrode combinations may help limit the amount of time required to select stimulation electrode combinations. The clinician may select a stimulation electrode combination based on a balance of side effects experienced by patient 12 and the extent to which the symptoms of the patient's movement disorder are mitigated. In these existing techniques, the clinician may not consider the specific anatomical make-up of brain 28 of patient 12 to select electrode combinations to test, nor the particular physiological characteristics of patient 12 or the particular dysfunctional state of the patient's brain 28. The existing techniques for selecting and testing stimulation electrode combinations and identifying a relatively efficacious stimulation electrode combination may be relatively time consuming and tedious.

In contrast, the systems, devices, and techniques described herein for selecting a stimulation electrode combination utilize information that is specific to patient 12. In particular, sensed bioelectrical brain signals may provide a clinician with useful information that indicates an efficacious stimulation electrode combination for patient 12. The information for selecting an efficacious stimulation electrode combination may be in the form of one or more frequency domain characteristics of a bioelectrical brain signal sensed by a particular sense electrode combination. The sensed bioelectrical brain signals are specific to patient 12 because they are sensed within the patient's brain 28, and, therefore, may be used to relatively quickly ascertain the stimulation electrode combinations that may provide efficacious therapy to the specific patient 12.

In addition to decreasing the time required to select an efficacious stimulation electrode combination, the techniques described herein may also help decrease amount of expertise or experience required to find an efficacious stimulation electrode combination in an efficient manner. For example, as described in further detail below with reference to FIG. 9, programmer 14 or another computing device may automatically evaluate one or more sense electrode combinations and determine which sense electrode combination is associated with a stimulation electrode combination that may provide efficacious therapy to patient 12 based on the bioelectrical brain signals specific to patient 12 and specific to the actual lead placement within the patient's brain 28.

After selecting electrode combinations in accordance with the systems and techniques described herein, a clinician, alone or with the aid of a computing device, such as programmer 14, may select the other stimulation parameter values that provide efficacious therapy to patient 12. These other stimulation parameter values may include, for example, a frequency and amplitude of stimulation signals, and, in the case of stimulation pulses, a duty cycle and pulse width of the stimulation signals.

In some examples, after IMD 16 is implanted within patient 12 and programmed for chronic therapy delivery, IMD 16 may periodically reassess the selected stimulation electrode combination to determine whether another stimulation electrode combination may provide more efficacious therapy. For example, a processor of IMD 16 may periodically sense bioelectrical brain signals with two or more sense electrode combinations comprising electrodes 24, 26 of leads 20A, 20B, respectively. The processor may determine whether stimulation should be delivered to brain 28 with a different stimulation electrode combination based on an analysis of the frequency band characteristics of the sensed bioelectrical brain signals. For example, the processor of IMD 16 may switch the subset of electrodes with which IMD 16 delivers stimulation to patient 12 if the currently selected stimulation electrode combination is not associated with a sense electrode combination that senses the bioelectrical brain signal having the relatively high relative beta band power. In this way, the stimulation electrode combination used by IMD 16 to deliver electrical stimulation to patient 12 may be dynamically changed in a closed-loop system.

Electrical stimulation generated by IMD 16 may be configured to manage a variety of disorders and conditions. In some examples, the stimulation generator of IMD 16 is configured to generate and deliver electrical pulses to patient 12 via electrodes of a selected stimulation electrode combination. However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may include a set of therapy parameter values, such as a stimulation electrode combination for delivering stimulation to patient 12, pulse frequency, pulse width, and a current or voltage amplitude of the pulses. As previously indicated, the stimulation electrode combination may indicate the specific electrodes 24, 26 that are selected to deliver stimulation signals to tissue of patient 12 and the respective polarity of the selected electrodes.

IMD 16 may be implanted within a subcutaneous pocket above the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic housing to substantially enclose components, such as a processor, therapy module, and memory.

Implanted lead extension 18 is coupled to IMD 16 via connector 30. In the example of FIG. 1, lead extension 18 traverses from the implant site of IMD 16 and along the neck of patient 12 to cranium 32 of patient 12 to access brain 28. In the example shown in FIG. 1, leads 20A and 20B (collectively "leads 20") are implanted within the right and left hemispheres, respectively, of patient 12 in order deliver electrical stimulation to one or more regions of brain 28, which may be selected based on the patient condition or disorder controlled by therapy system 10. Other lead 20 and IMD 16 implant sites are contemplated. For example, IMD 16 may be implanted on or within cranium 32, in some examples. Or leads 20 may be implanted within the same hemisphere or IMD 16 may be coupled to a single lead.

Although leads 20 are shown in FIG. 1 as being coupled to a common lead extension 18, in other examples, leads 20 may be coupled to IMD 16 via separate lead extensions or directly to connector 30. Leads 20 may be positioned to deliver electrical stimulation to one or more target tissue sites within brain 28 to manage patient symptoms associated with a movement disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, electrodes 24, 26 may be surgically implanted under the dura mater of brain 28 or within the cerebral cortex of brain 28 via a burr hole in cranium 32 of patient 12, and electrically coupled to IMD 16 via one or more leads 20.

Example techniques for delivering therapy to manage a movement disorder are described in U.S. Pat. No. 8,121,694 to Molnar et al., entitled, "THERAPY CONTROL BASED ON A PATIENT MOVEMENT STATE," which issued on Feb. 21, 2012, and is incorporated herein by reference in its entirety. In some examples described by U.S. Pat. No. 8,121, 694 to Molnar et al., a brain signal, such as an EEG or ECoG signal, may be used to determine whether a patient is in a movement state or a rest state. The movement state includes the state in which the patient is generating thoughts of movement (i.e., is intending to move), attempting to initiate movement or is actually undergoing movement. The movement state or rest state determination may then be used to control therapy delivery. For example, upon detecting a movement state of the patient, therapy delivery may be activated in order to help patient 12 initiate movement or maintain movement, and upon detecting a rest state of patient 12, therapy delivery may be deactivated or otherwise modified.

In the example shown in FIG. 1, electrodes 24, 26 of leads 20 are shown as ring electrodes. Ring electrodes may be used in DBS applications because they are relatively simple to program and are capable of delivering an electrical field to any tissue adjacent to electrodes 24, 26. In other examples, electrodes 24, 26 may have different configurations. For examples, in some examples, at least some of the electrodes 24, 26 of leads 20 may have a complex electrode array geometry that is capable of producing shaped electrical fields. The complex electrode array geometry may include multiple electrodes (e.g., partial ring or segmented electrodes) around the outer perimeter of each lead 20, rather than one ring electrode. In this manner, electrical stimulation may be directed to a specific direction from leads 20 to enhance therapy efficacy and reduce possible adverse side effects from stimulating a large volume of tissue. In some examples, a housing of IMD 16 may include one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 12.

Figure 3:
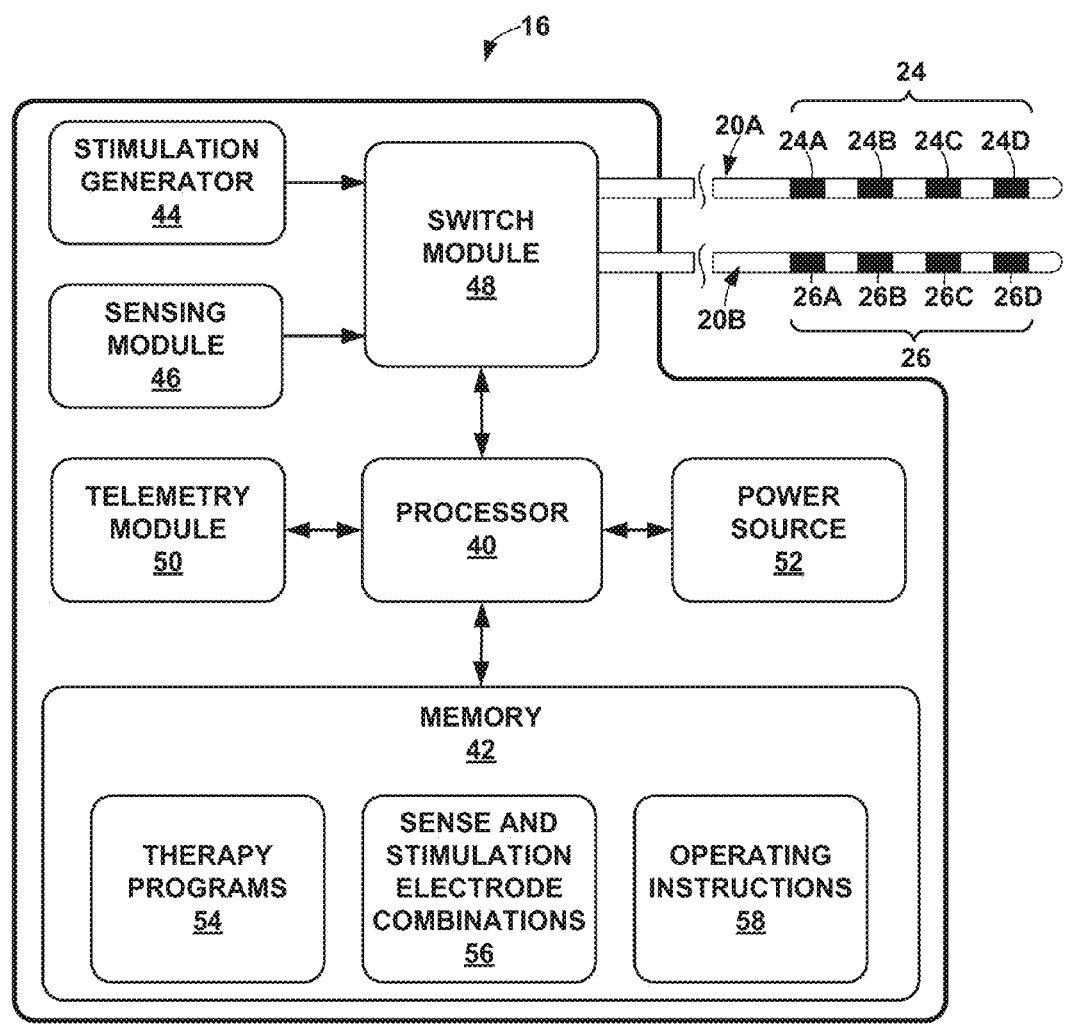
FIG. 3 is functional block diagram illustrating components of an example medical device.

In the example shown in FIG. 3, IMD 16 includes a memory 42 to store a plurality of therapy programs 54 that each defines a set of therapy parameter values. In some examples, IMD 16 may select a therapy program from memory 42 based on various parameters, such as a detected patient activity level, a detected patient state, based on the time of day, and the like. IMD 16 may generate electrical stimulation based on the selected therapy program to manage the patient symptoms associated with a movement disorder.

During a trial stage in which IMD 16 is evaluated to determine whether IMD 16 provides efficacious therapy to patient 12, a plurality of therapy programs may be tested and evaluated for efficacy. In addition, one or more stimulation electrode combinations may be selected for the one or more therapy programs based on frequency band characteristics of sensed bioelectrical brain signals, as described in further detail below. Therapy programs may be selected for storage within IMD 16 based on the results of the trial stage.

During chronic therapy in which IMD 16 is implanted within patient 12 for delivery of therapy on a non-temporary basis, IMD 16 may generate and deliver stimulation signals to patient 12 according to different therapy programs 54. In addition, in some examples, patient 12 may modify the value of one or more therapy parameter values within a single given program or switch between programs in order to alter the efficacy of the therapy as perceived by patient 12 with the aid of programmer 14. Memory 42 of IMD 16 may store instructions defining the extent to which patient 12 may adjust therapy parameters, switch between programs, or undertake other therapy adjustments. Patient 12 may generate additional programs for use by IMD 16 via external programmer 14 at any time during therapy or as designated by the clinician.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20 and the electrode arrangement, the position of leads 20 within brain 28, the configuration of electrode array 24, 26, initial programs defining therapy parameter values, and any other information the clinician desires to program into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that may provide efficacious therapy to patient 12 to address symptoms associated with one or more different patient states, such as a sleep state, movement state or rest state. For example, the clinician may select one or more stimulation electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient (e.g., muscle activity or muscle tone). Programmer 14 may assist the clinician in the creation/identification of therapy programs by providing a methodical system for identifying potentially beneficial therapy parameter values.

As described in commonly-assigned U.S. Patent Application Publication No. 2009/0192556 by Jianping Wu et al., entitled, "SLEEP STAGE DETECTION," which was filed on Sep. 25, 2008 and published on Jul. 30, 2009, and is incorporated herein by reference in its entirety, a particular sleep stage of a patient's sleep state may be detected based on a frequency characteristic of a biosignal from a brain of the patient. The frequency characteristic of the biosignal may include, for example, a power level (or energy) within one or more frequency bands of the biosignal, a ratio of the power level in two or more frequency bands, a correlation in change of power between two or more frequency bands, a pattern in the power level of one or more frequency bands over time, and the like. Example sleep stages include, for example, Stage 1 (also referred to as Stage N1 or S1), Stage 2 (also referred to as Stage N2 or S2), Deep Sleep (also referred to as slow wave sleep), and rapid eye movement (REM). The Deep Sleep stage may include multiple sleep stages, such as Stage N3 (also referred to as Stage S3) and Stage N4 (also referred to as Stage S4). In some cases, patient 12 may cycle through the Stage 1, Stage 2, Deep Sleep, REM sleep stages more than once during a sleep state. The Stage 1, Stage 2, and Deep Sleep stages may be considered non-REM (NREM) sleep stages.

Therapy delivered to patient 12 during the sleep state may be controlled based on a determined sleep stage. For example, a therapy program may be selected based on the detected sleep stage or a therapy program may be modified based on the detected sleep stage. Therapy to the patient during the detected sleep stage may be delivered according to the selected or modified therapy program. The stored therapy programs 54 may be, for example, associated with different sleep stages.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

FIG. 3 is a functional block diagram illustrating components of an example IMD 16. In the example shown in FIG. 3, IMD 16 includes processor 40, memory 42, stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions.

As previously discussed, in the example shown in FIG. 3, memory 42 stores therapy programs 54, sense electrode combinations and associated stimulation electrode combinations 56, and operating instructions 58 in separate memories within memory 42 or separate areas within memory 42. In addition, in some examples, memory 42 may store a bioelectrical brain signal sensed via at least some of the stored sense electrode combinations and/or one or more frequency band characteristics of the bioelectrical brain signals. Each stored therapy program 52 defines a particular program of therapy in terms of respective values for electrical stimulation parameters, such as a stimulation electrode combination, electrode polarity, current or voltage amplitude, pulse width, and pulse rate. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 56 stores sense electrode combinations and associated stimulation electrode combinations. As described above, in some examples, the sense and stimulation electrode combinations may include the same subset of electrodes 24, 26, or may include different subsets of electrodes. Operating instructions 58 guide general operation of IMD 16 under control of processor 40, and may include instructions for measuring the impedance of electrodes 24, 26 and/or determining the distance between electrodes 24, 26.

Stimulation generator 44, under the control of processor 40, generates stimulation signals for delivery to patient 12 via selected combinations of electrodes 24, 26. An example range of electrical stimulation parameters believed to be effective in DBS to manage a movement disorder of patient include:

1. Frequency: between approximately 100 Hz and approximately 500 Hz, such as approximately 130 Hz.
2. Voltage Amplitude: between approximately 0.1 volts and approximately 50 volts, such as between approximately 0.5 volts and approximately 20 volts, or approximately 5 volts.
3. Current Amplitude: A current amplitude may be defined as the biological load in which the voltage is delivered. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kiloohms.
4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 44 generates electrical stimulation signals in accordance with the electrical stimulation parameters noted above. Other ranges of therapy parameter values may also be useful, and may depend on the target stimulation site within patient 12, which may or may not be within brain 28. While stimulation pulses are described, stimulation signals may be of any form, such as continuous-time signals (e.g., sine waves) or the like.

In each of the examples described herein, if stimulation generator 44 shifts the delivery of stimulation energy between two therapy programs, processor 40 of IMD 16 may provide instructions that cause stimulation generator 44 to time-interleave stimulation energy between the electrode combinations of the two therapy programs, as described in commonly-assigned U.S. Pat. No. 7,519,431 to Steven Goetz et al., entitled, "SHIFTING BETWEEN ELECTRODE COMBINATIONS IN ELECTRICAL STIMULATION DEVICE," and issued on Apr. 14, 2009, the entire content of which is incorporated herein by reference. In the time-interleave shifting example, the amplitudes of the electrode combinations of the first and second therapy program are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off. Other techniques for shifting the delivery of stimulation signals between two therapy programs may be used in other examples.

Processor 40 may include any one or more of a microprocessor, a controller, a digital signal processor (DSP), an application specific integrated circuit (ASIC), a field-programmable gate array (FPGA), discrete logic circuitry, and the functions attributed to processor 40 herein may be embodied as firmware, hardware, software or any combination thereof. Processor 40 controls stimulation generator 44 according to therapy programs 52 stored in memory 42 to apply particular stimulation parameter values specified by one or more of programs, such as amplitude, pulse width, and pulse rate.

In the example shown in FIG. 3, the set of electrodes 24 includes electrodes 24A, 24B, 24C, and 24D, and the set of electrodes 26 includes electrodes 26A, 26B, 26C, and 26D. Processor 40 also controls switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 46 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 46 and conductors within leads 20. In some examples, however, IMD 16 does not include switch module 46.

Stimulation generator 44 may be a single channel or multi-channel stimulation generator. In particular, stimulation generator 44 may be capable of delivering, a single stimulation pulse, multiple stimulation pulses or continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

As described in further detail with reference to FIG. 9, in some examples, processor 40 may dynamically change the selected combinations of electrodes 24, 26, i.e., the stimulation electrode combination, based on one or more frequency domain characteristics of bioelectrical signals sensed within brain 28. Sensing module 46, under the control of processor 40, may sense bioelectrical brain signals and provide the sensed bioelectrical brain signals to processor 40. Processor 40 may control switch module 48 to couple sensing module 46 to a selected combinations of electrodes 24, 26, i.e., a sense electrode combination. In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signal sensed across the selected electrodes 24, 26 to sensing module 46. The bioelectrical brain signal may include electrical signals that are indicative of electrical activity within brain 28 of patient 12.

Although sensing module 46 is incorporated into a common housing with stimulation generator 44 and processor 40 in FIG. 3, in other examples, sensing module 46 may be in a separate housing from IMD 16 and may communicate with processor 40 via wired or wireless communication techniques. Example bioelectrical brain signals include, but are not limited to, a signal generated from local field potentials within one or more regions of brain 28. EEG and ECoG signals are examples of local field potentials that may be measured within brain 28. However, local field potentials may include a broader genus of electrical signals within brain 28 of patient 12.

Processor 40 may analyze the bioelectrical brain signal, e.g., a frequency domain characteristic of the biosignal, to evaluate different stimulation electrode combinations. As previously indicated, a stimulation electrode combination may be associated with a sense electrode combination in memory 42. Processor 40 may evaluate different stimulation electrode combinations by, at least in part, sensing bioelectrical brain signals with the sense electrode combination associated with a respective one of the stimulation electrode combinations and analyzing a frequency domain characteristic of the sensed bioelectrical brain signal.

A frequency domain characteristic of the biosignal may include, for example, a power level (or energy) within one or more frequency bands of the biosignal, a ratio of the power level in two or more frequency bands, a correlation in change of power between two or more frequency bands, a pattern in the power level of one or more frequency bands over time, and the like. In some examples, as described with reference to FIG. 5, processor 40 may adjust a stimulation electrode combination or otherwise select a stimulation electrode combination by selecting a stimulation electrode combination that is associated with the sense electrode combination that sensed the bioelectrical brain signal comprising the greatest relative beta band power compared to the other sensed bioelectrical brain signals. In other examples, processor 40 may select a stimulation electrode combination that is associated with the sense electrode combination that sensed a bioelectrical brain signal comprising a power level in a particular frequency band above a threshold value, which may be stored in memory 42.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by radiofrequency (RF) communication techniques. In addition, telemetry module 50 may communicate with external medical device programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 4:
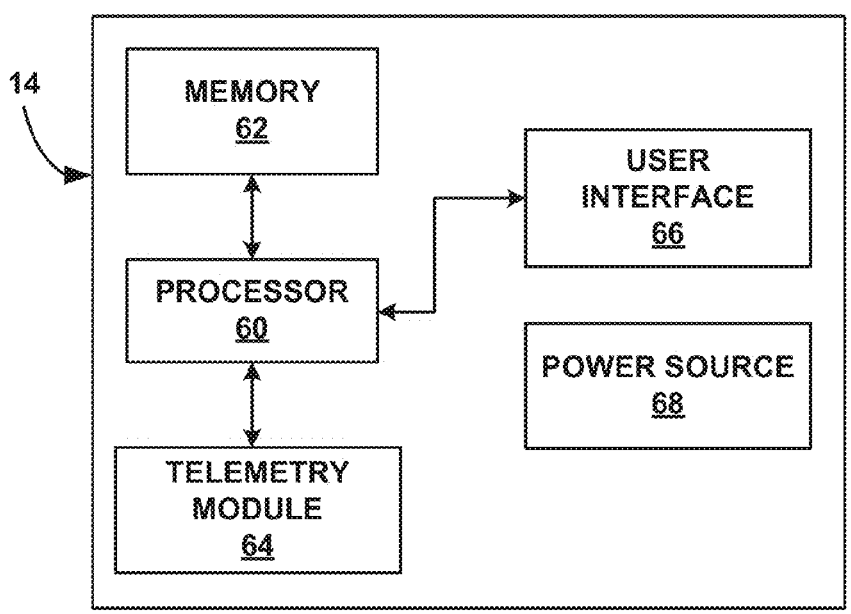
FIG. 4 is a functional block diagram illustrating components of an example medical device programmer.

FIG. 4 is a conceptual block diagram of an example external medical device programmer 14, which includes processor 60, memory 62, telemetry module 64, user interface 66, and power source 68. Processor 60 controls user interface 66 and telemetry module 64, and stores and retrieves information and instructions to and from memory 62. Programmer 14 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

A user, such as a clinician or patient 12, may interact with programmer 14 through user interface 66. User interface 66 includes a display (not shown), such as a LCD or LED display or other type of screen, to present information related to the therapy, such as information related to bioelectrical signals sensed via a plurality of sense electrode combinations. In addition, user interface 66 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 60 of programmer 14 and provide input.

If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display. In other examples, user interface 66 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 60 of programmer 14. For example, in some examples, processor 60 may receive a bioelectrical brain signal from IMD 16 or from a sensing module that is separate from IMD 16. The separate sensing module may, but need not be, implanted within patient 12. In some examples, processor 60 may evaluate one or more stimulation electrode combinations based on a frequency component of a bioelectrical brain signals sensed with the one or more sense electrode combinations associated with at least one of the stimulation electrode combinations. Processor 60 may select a stimulation electrode combination for IMD 16 based on the analysis of the frequency domain characteristics of the sensed bioelectrical brain signals. In some cases, processor 60 may transmit a signal to IMD 16 to instruct IMD 16 to switch stimulation electrode combinations.

Processor 40 of IMD 16 may receive the signal from programmer 14 via its respective telemetry module 50 (FIG. 3). Processor 40 of IMD 16 may switch stimulation electrode combinations by selecting a stored therapy program from memory 42 based on the signal from processor 60 of programmer 14. Alternatively, processor 60 of programmer 14 may select a therapy program or a specific stimulation electrode combination and transmit a signal to IMD 16, where the signal indicates the therapy parameter values to be implemented by IMD 16 to help improve the efficacy of the stimulation to manage the patient's movement disorder. The indication may be, for example, an alphanumeric identifier or symbol that is associated with the therapy program in memory 42 of IMD 16.

Memory 62 may include instructions for operating user interface 66 and telemetry module 64, and for managing power source 68. Memory 62 may also store any therapy data retrieved from IMD 16 during the course of therapy. The clinician may use this therapy data to determine the progression of the patient condition in order to predict future treatment. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 64. Accordingly, telemetry module 64 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 delivers operating power to the components of programmer 14. Power source 68 may include a battery and a power generation circuit to produce the operating power. In some examples, the battery may be rechargeable to allow extended operation. Recharging may be accomplished by electrically coupling power source 68 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 68 may include circuitry to monitor power remaining within a battery. In this manner, user interface 66 may provide a current battery level indicator or low battery level indicator when the battery needs to be replaced or recharged. In some cases, power source 68 may be capable of estimating the remaining time of operation using the current battery.

Figure 5:
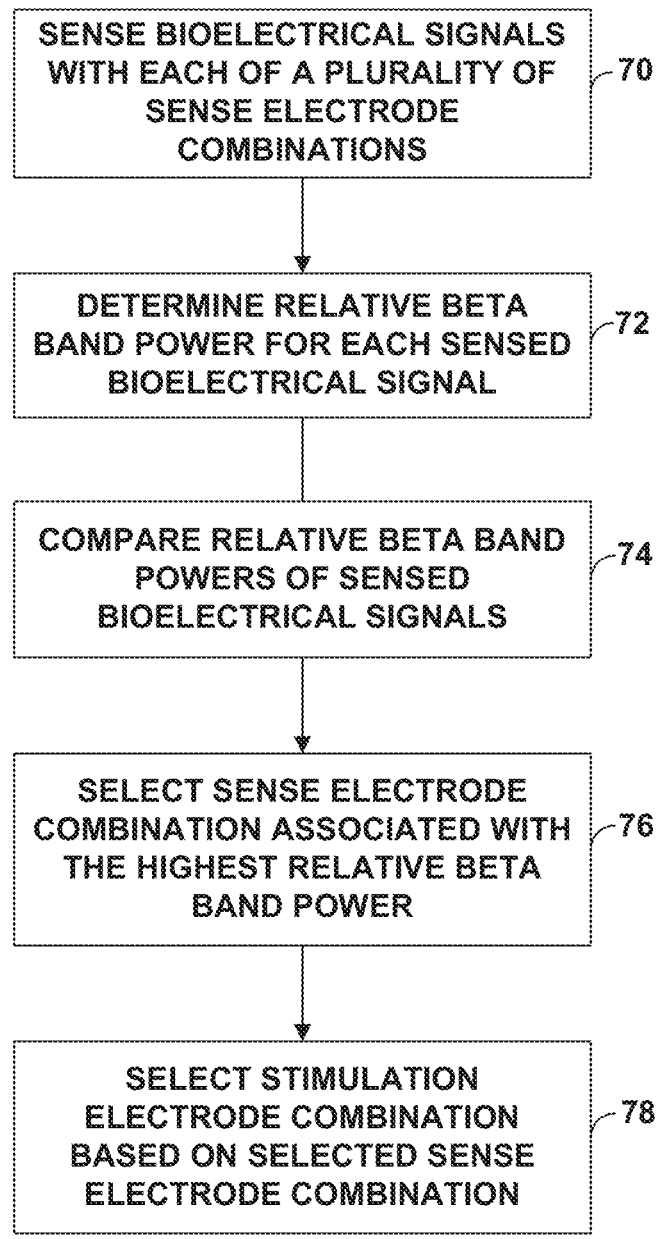
FIG. 5 is a flow diagram of an example technique for selecting a stimulation electrode combination based on a frequency domain characteristic of a bioelectrical signal sensed via a sense electrode combination.
Figure 7:
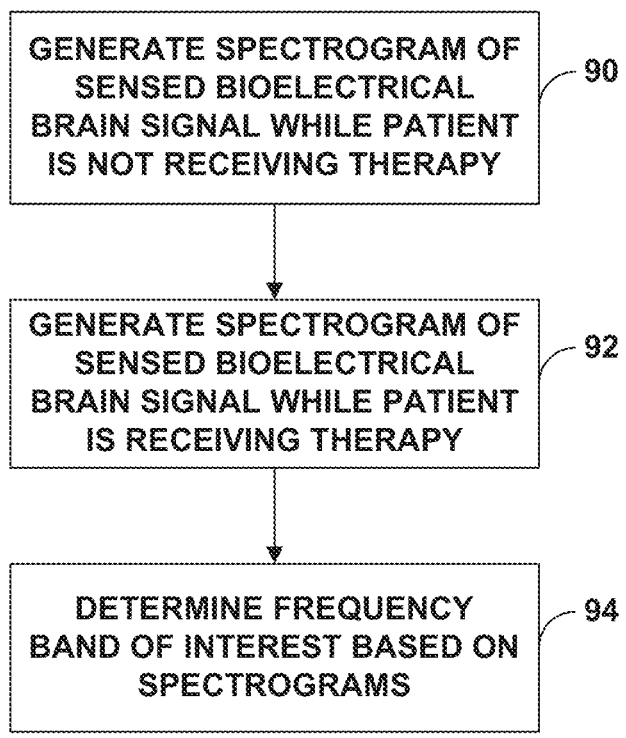
FIG. 7 is a flow diagram of an example technique for determining a frequency band of interest for evaluating sense electrode combinations.
Figure 10:
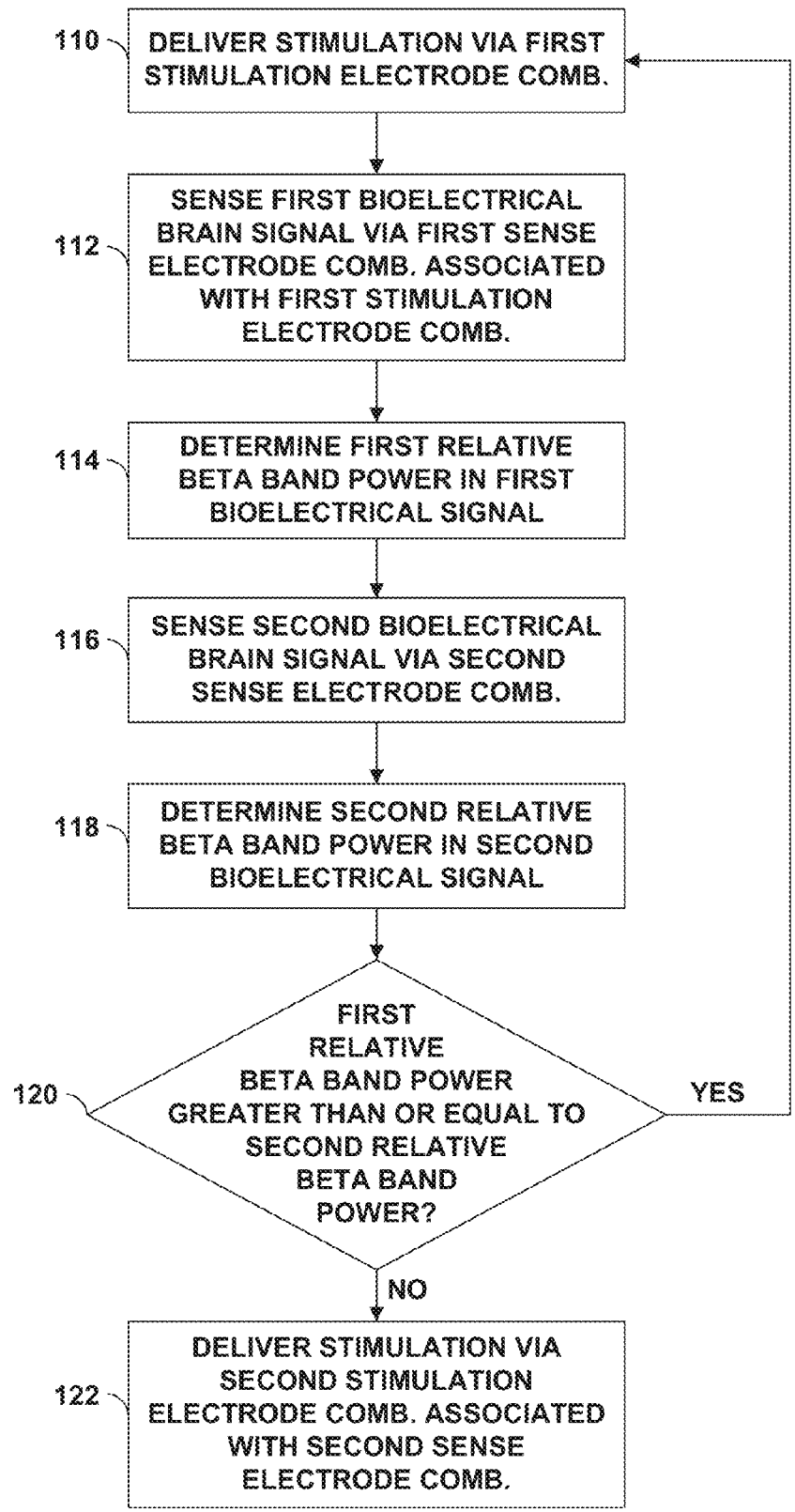
FIG. 10 is a flow diagram of an example technique for evaluating a stimulation electrode combination.

FIG. 5 is a flow diagram illustrating an example technique that processor 40 of IMD 16 may implement in order to select a stimulation electrode combination for delivering efficacious stimulation therapy to brain 28 of patient 12. While FIG. 5, as well as FIGS. 7 and 10, are primarily described with reference to processor 40 of IMD 16, in other examples, processor 60 of programmer 14 or a processor of another computing device may perform any one or more parts of the techniques described herein, such as the techniques described with reference to FIGS. 5, 7, and 10.

Processor 40 of IMD 16 may control sensing module 46 (FIG. 3) to sense bioelectrical brain signals with each of a plurality of sense electrode combinations (70). For example, switch module 48 (FIG. 3), under the control of processor 40, may selectively couple sensing module 46 to a first subset of electrodes 24, 26, and sensing module 46 may sense a first local field potential within brain 28 via the first subset of electrodes 24, 26. This first subset of electrodes may also be referred to as a first sense electrode combination. Processor 40 may store the first bioelectrical brain signal resulting from the measurement of the first local field potential within brain 28 via the first subset of electrodes 24, 26 within memory 42 of IMD 16.

Sensing module 48 may subsequently selectively couple sensing module 46 to a second subset of electrodes 24, 26, i.e., a second sense electrode combination, which differs from the first subset by at least one electrode. Sensing module 46 may sense a local field potential within brain 28 via the second subset of electrodes 24, 26. Processor 40 may store the second bioelectrical brain signal resulting from the measurement of the local field potential within brain 28 via the second subset of electrodes 24, 26 within memory 42 of IMD 16. Processor 40 may continue sensing bioelectrical brain signals within brain 28 with any suitable number of sense electrode combinations. The sense electrode combinations may be stored in memory 42 of IMD 16 or a memory of another device.

Processor 40 may determine a relative beta band power of each sensed bioelectrical brain signal (72). In some examples, sensing module 46 may include circuitry to tune to and extract a power level of a particular frequency band of a sensed bioelectrical brain signal. Thus, the power level of a particular frequency band of a sensed bioelectrical brain signal may be extracted prior to digitization of the signal by processor 40. By tuning to and extracting the power level of a particular frequency band before the signal is digitized, it may be possible to run frequency domain analysis algorithms at a relatively slower rate compared to systems that do not include a circuit to extract a power level of a particular frequency band of a sensed bioelectrical brain signal prior to digitization of the signal. In some examples, sensing module 46 may include more than one channel to monitor simultaneous activity in different frequency bands, i.e., to extract the power level of more than one frequency band of a sensed bioelectrical brain signal. These frequency bands may include a beta frequency band, e.g., approximately 10 Hz to approximately 30 Hz, such as about 20 Hz, or other frequency bands.

In some examples, sensing module 46 of IMD 16 may include an architecture that merges chopper-stabilization with heterodyne signal processing to support a low-noise amplifier. In some examples, sensing module 46 may include a frequency selective signal monitor that includes a chopper-stabilized superheterodyne instrumentation amplifier and a signal analysis unit. Example amplifiers that may be included in the frequency selective signal monitor are described in further detail in commonly-assigned U.S. Patent Application Publication No. 2009/0082691 by Denison et al., entitled, "FREQUENCY SELECTIVE MONITORING OF PHYSIOLOGICAL SIGNALS" which was filed on Sep. 25, 2008 and published on Mar. 26, 2009. U.S. Patent Application Publication No. 2009/0082691 by Denison et al. is incorporated herein by reference in its entirety.

As described in U.S. Patent Application Publication No. 2009/0082691 by Denison et al., frequency selective signal monitor may utilize a heterodyning, chopper-stabilized amplifier architecture to convert a selected frequency band of a physiological signal to a baseband for analysis. The physiological signal may include a bioelectrical brain signal, which may be analyzed in one or more selected frequency bands to select a stimulation electrode combination in accordance with the techniques described herein. The frequency selective signal monitor may provide a physiological signal monitoring device comprising a physiological sensing element that receives a physiological signal, an instrumentation amplifier comprising a modulator that modulates the signal at a first frequency, an amplifier that amplifies the modulated signal, and a demodulator that demodulates the amplified signal at a second frequency different from the first frequency. A signal analysis unit may analyze a characteristic of the signal in the selected frequency band. The second frequency may be selected such that the demodulator substantially centers a selected frequency band of the signal at a baseband.

Different movement disorder symptoms may be detected in different frequency bands of a bioelectrical brain signal. An example of frequency bands is shown in Table 1 below:

TABLE 1

| Frequency (f) Band Hertz (Hz) | Frequency Information |
| --- | --- |
| f < 5 Hz | δ (delta frequency band) |
| 5 Hz ≤ f ≤ 10 Hz | α (alpha frequency band) |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

Processor 40 may select the frequency band to monitor based on the patient's symptoms. As previously indicated, activity of the sensed bioelectrical brain signal within a beta band may be associated with bradykinesia of patient 12. Other symptoms of the patient's movement disorder may be associated with the energy of a bioelectrical brain signal within other frequency bands, such as the alpha or high gamma bands.

A relative beta band power may include a ratio of a power level in the beta frequency band of a sensed bioelectrical brain signal to the overall power of the sensed bioelectrical brain signal. The power level in the beta band may be determined using any suitable technique. In some examples, processor 40 may average the power level of the beta band of a sensed bioelectrical brain signal over a predetermined time period, such as about ten seconds to about two minutes, although other time ranges are also contemplated. In other examples, the beta band power level may be a median power level over a predetermined range of time, such as about ten seconds to about two minutes. The activity within the beta band of a bioelectrical brain signal, as well as other frequency bands of interest, may fluctuate over time. Thus, the power level in the selected frequency band at one instant in time may not provide an accurate and precise indication of the energy of the bioelectrical brain signal in the selected frequency band. Averaging or otherwise monitoring the power level in the selected frequency band over time may help capture a range of power levels, and, therefore, a better indication of the patient's pathological state in the particular brain region sensed by the selected sense electrode combination.

The overall power of the sensed bioelectrical brain signal may be determined using any suitable technique. In one example, processor 40 may determine an overall power level of a sensed bioelectrical brain signal based on the total power level of a swept spectrum of the bioelectrical brain signal. To generate the swept spectrum, processor 40 may control sensing module 46 to tune to consecutive frequency bands over time, and processor 40 may assemble a pseudo-spectrogram of the sensed bioelectrical brain signal based on the power level in each of the extracted frequency bands. The pseudo-spectrogram may be indicative of the energy of the frequency content of the bioelectrical brain signal within a particular window of time.

In one accordance with example technique, processor 40 may determine an overall power level of a sensed bioelectrical brain signal based on time domain data. For example, processor 40 may determine the relative beta band power by determining a ratio of the beta band power to a voltage amplitude of the signal. The voltage amplitude may be a mean or median voltage amplitude of the signal over a predetermined range of time, such as about ten seconds to about two minutes, although other time ranges are also contemplated. The voltage amplitudes of the bioelectrical brain signals may be calibration coefficients that help minimize variability between the power levels of the bioelectrical brain signals in a particular frequency band that is attributable to differences in the overall signal power level.

Processor 40 may compare the relative beta band power levels of the sensed bioelectrical brain signals (74). Comparing the relative beta band power levels of the bioelectrical brain signals may be more meaningful than comparing the absolute beta band power levels because the signal strength may change depending on the electrodes used to sense the bioelectrical brain signal. A sensed bioelectrical brain signal having a higher overall signal strength may appear to have a higher beta band power level than a second sensed bioelectrical brain signal having a lower overall signal strength, even though the second sensed bioelectrical signal may have a higher relative beta power.

For example, if a first sense electrode combination includes electrodes 24A, 24D and a second sense electrode combination includes electrodes 24A, 24B, a first bioelectrical brain signal sensed via the first sense electrode combination may have a greater overall signal strength, and, therefore, a greater beta band power level than a second bioelectrical brain signal sensed via the second sense electrode combination due to distance between the electrodes of the first and second sense electrode combinations. Comparing the relative beta band power levels may reduce the variability in the measured beta band power levels of the sensed bioelectrical signals attributable to variability in the overall signal strength.

After comparing the relative beta band powers of the sensed bioelectrical brain signals (74), processor 40 may select the sense electrode combination that is associated with the highest relative beta band power (76). Processor 40 may select a stimulation electrode combination based on the selected sense electrode combination (78). As previously indicated, memory 42 of IMD 16 may store information associating sense and stimulation electrode combinations 56 (FIG. 3). In some examples, the sense electrode combination and stimulation electrode combination may comprise the same subset of electrodes 24, 26, while in other examples, the sense and stimulation electrode combinations may comprise different subsets of electrodes 24, 26.

Figure 6A:
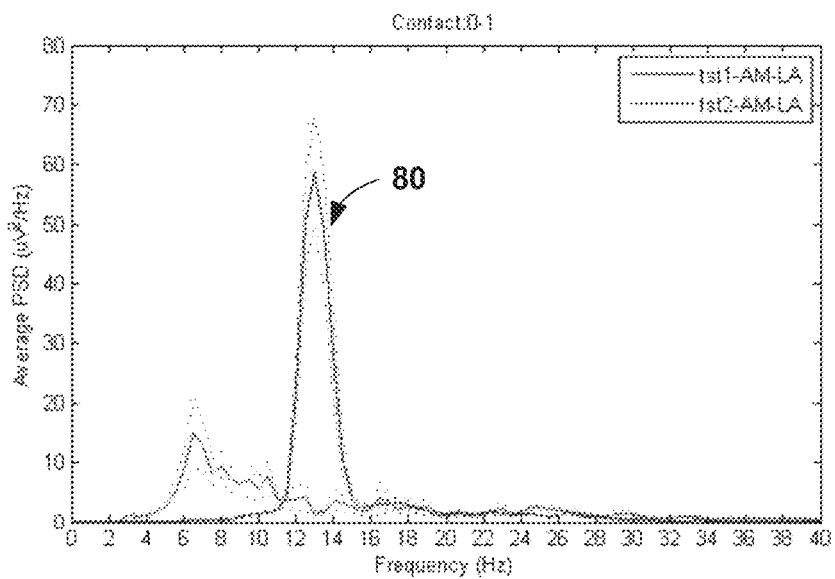
FIGS. 6A-6D are conceptual power spectral density (PSD) plots of bioelectrical brain signals sensed via different sense electrode combinations.
Figure 6B:
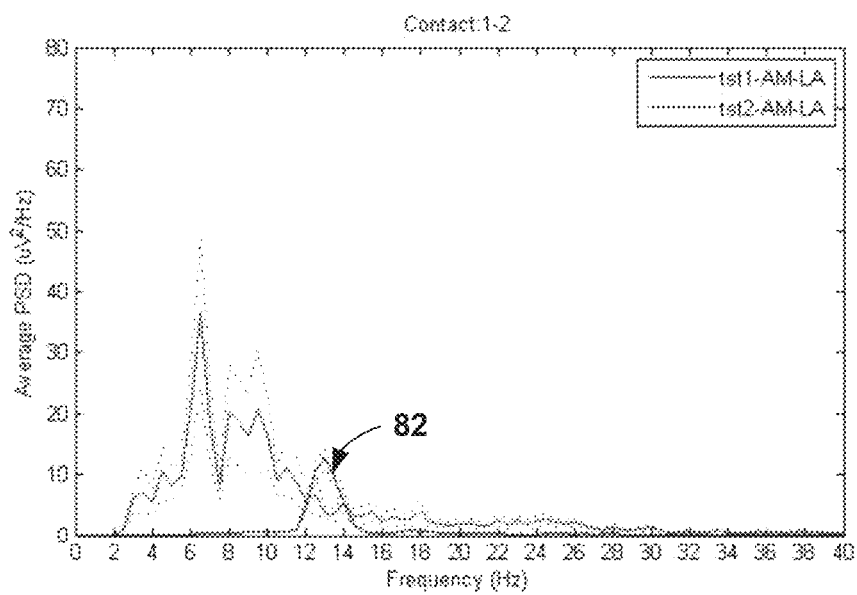

FIGS. 6A-6D are example power spectral density (PSD) plots of bioelectrical brain signals sensed via different sense electrode combinations. The average PSD is shown in microvolts squared per Hertz ($\mu v^2$/Hz). FIG. 6A illustrates a PSD plot of a first bioelectrical brain signal 80 sensed via a first sense electrode combination including electrodes 24D, 24C of lead 20A (FIG. 3). As shown in FIG. 6A, a greatest power level of the first bioelectrical signal 80 in a beta band (approximately 10 Hz to about 20 Hz) is approximately 58 $\mu v^2$/Hz. FIG. 6B illustrates a PSD plot of a second bioelectrical brain signal 82 sensed via a second sense electrode combination including electrodes 24C, 24B of lead 20A (FIG. 3). As shown in FIG. 6B, a greatest power level of the second bioelectrical signal 82 in a beta band is approximately 12 $\mu v^2$/Hz.

Figure 6C:
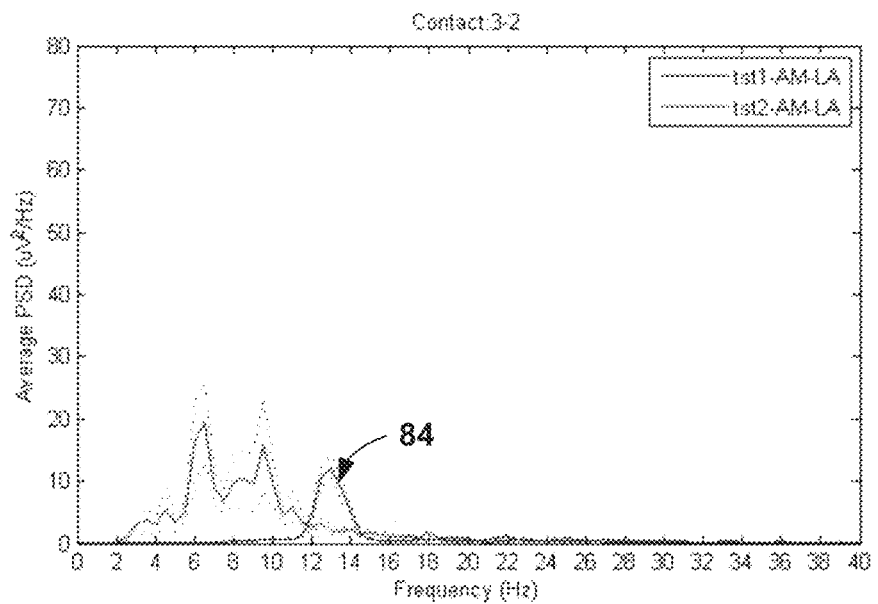
Figure 6D:
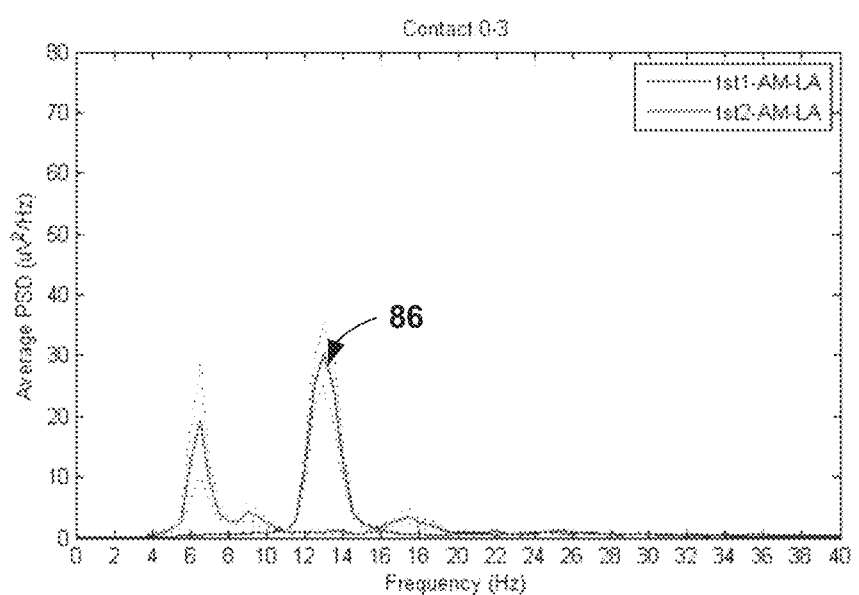

FIG. 6C illustrates a PSD plot of a third bioelectrical brain signal 84 sensed via a third sense electrode combination including electrodes 24B, 24A of lead 20A (FIG. 3). As shown in FIG. 6C, a greatest power level of the third bioelectrical signal 84 in a beta band is approximately 11 $\mu v^2$/Hz. FIG. 6D illustrates a PSD plot of a fourth bioelectrical brain signal 86 sensed via a fourth sense electrode combination including electrodes 24B, 24A of lead 20A (FIG. 3). As shown in FIG. 6D, a greatest power level of the fourth bioelectrical signal 86 in a beta band is approximately 30 $\mu v^2$/Hz.

If the sensed bioelectrical brain signals 80, 82, 84, 86 shown in FIGS. 6A-6D, respectively, have substantially similar overall power levels, processor 40 may determine that first bioelectrical brain signal 80 has the highest relative beta band power. Accordingly, processor 40 may select a stimulation electrode combination based on the first sense electrode combination by reference memory 42 of IMD 16. As previously indicated, memory 42 may store information associating sense electrode combinations with stimulation electrode combinations.

In some examples, processor 40 may identify an efficacious stimulation electrode combination for therapy delivery to patient 12 based on a frequency band of a bioelectrical brain signal other than a beta band. FIG. 7 is a flow diagram of an example technique that processor 40 of IMD 16, processor 60 of programmer 14, or another computing device may implement to identify a frequency band of interest. Processor 40 is referred to throughout the description of FIG. 7. In other examples, processor 60 of programmer 14 or another computing device may implement the technique shown in FIG. 7 to identify a frequency band of interest.

Processor 40 may generate a spectrogram (e.g., as shown in FIG. 2) of a bioelectrical brain signal of patient 12 during a first time period in which patient 12 is in a pathological state, e.g., is not receiving any therapy to manage the movement disorder or other patient condition (90). Processor 40 may generate a spectrogram during a second time period in which patient 12 is receiving therapy to manage the movement disorder or other patient condition (92). Processor 40 may determine a frequency band of interest that indicates a biomarker for the patient's condition based on the spectrograms (94). In some examples, processor 40 may determine which frequency bands exhibited a relatively large and/or discernable change between the first and second time periods. For example, in the spectrogram shown in FIG. 2, the beta band activity decreased after the human subject began receiving a pharmaceutical agent to manage a movement disorder, as indicated by time period 38.

Processor 40 may utilize the frequency band of interest in order to identify a stimulation electrode combination in accordance with the techniques described herein. In some examples, processor 40 may sense bioelectrical brain signals within brain 28 of patient 12 with each sense electrode combination of a plurality of stored sense electrode combinations. Processor 40 may select a stimulation electrode combination based on the sense electrode combination associated with a sensed bioelectrical brain signal having a greatest relative power level in the frequency band of interest. In other examples, processor 40 may select a stimulation electrode combination based on the sense electrode combination associated with a sensed bioelectrical brain signal having a lowest relative power level in the frequency band of interest.

Figure 8:
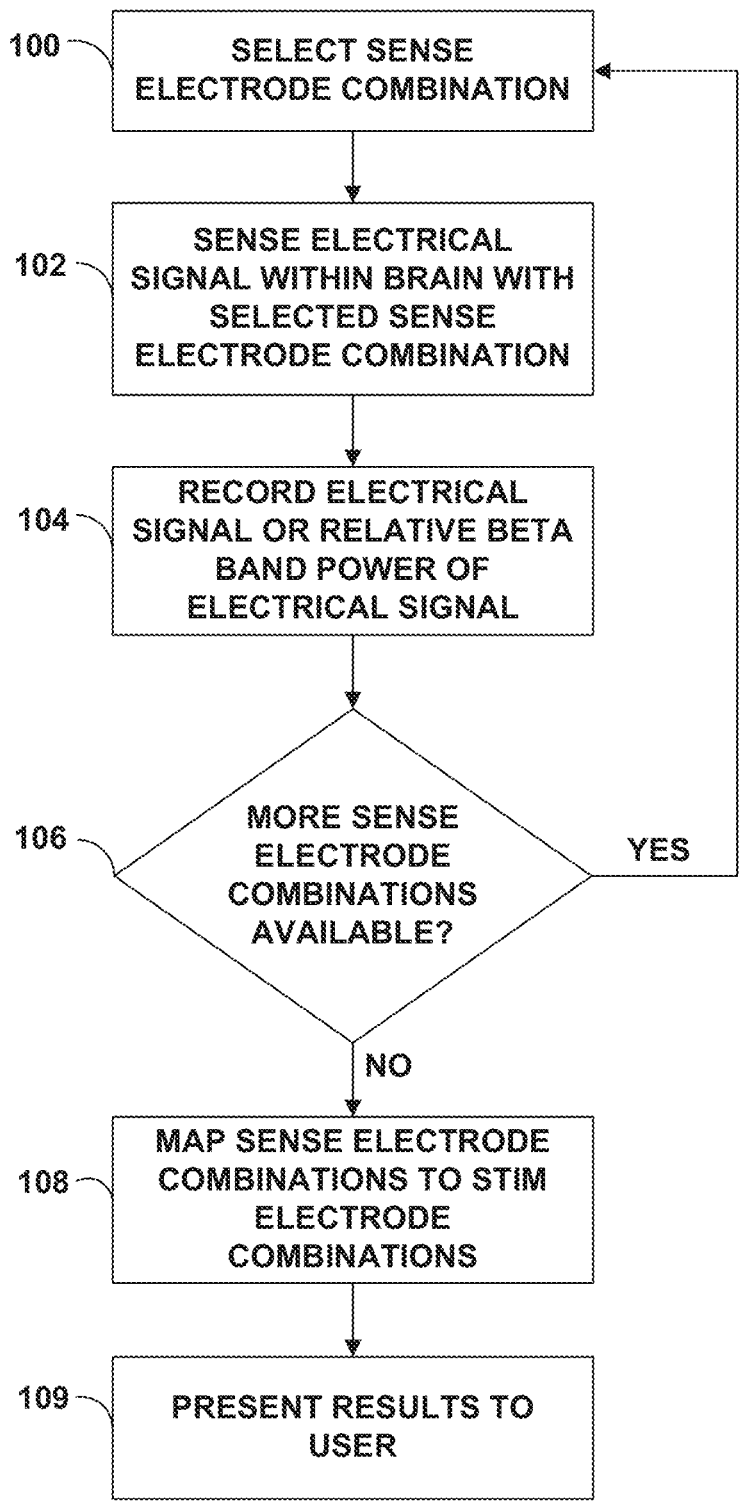
FIG. 8 is a flow diagram of an example technique for evaluating frequency domain characteristics of various sense electrode combinations.

In some examples, the different sense electrode combinations and associated beta band power levels may be presented to a user, such as a clinician, via a display of a device, such as programmer 14. FIG. 8 is a flow diagram of an example technique that processor 60 of programmer 14 may implement in order to determine the beta band power levels of bioelectrical brain signals sensed via a respective one of a plurality of sense electrode combinations. In other examples, processor 40 of IMD 16 or another device may perform any part of the technique shown in FIG. 8.

Processor 60 may select a sense electrode combination from memory 62 (FIG. 4) of programmer 14 (100). Memory 62 may store any number of sense electrode combinations, which may include, for example, every possible combination of electrodes 24, 26 implanted within patient 12 that may be used to sense electrical activity within brain 28. Processor 60 may control IMD 16 to sense a bioelectrical brain signal with the selected sense electrode combination (102). For example, via the respective telemetry modules 64, 50, processor 60 may provide a signal to processor 40 of IMD 16 that indicates that processor 40 should controls sensing module 46 (FIG. 3) to initiate the measurement of a local field potential within brain 28 via the electrodes of the selected sense electrode combination. Processor 60 may also transmit the sense electrode combination to processor 40, such as providing a signal indicating the subset of electrodes 24, 26 in the sense electrode combination or by providing a signal indicating an identifier associated with the selected sense electrode combination. IMD 16 may store sense electrode combinations within memory 42 and associate each sense electrode combination with an identifier, such as an alphanumeric identifier.

Processor 60 may receive the sensed bioelectrical brain signal from processor 40 of IMD 16 via the respective telemetry modules 64, 50 (FIGS. 3 and 4), and record the bioelectrical brain signal in memory 62 of programmer 14 (104). In some examples, instead of or in addition to the bioelectrical brain signal, processor 60 may record the relative beta band power of the sensed bioelectrical brain signal in memory 62. After sensing and recording the bioelectrical brain signal with a first sense electrode combination, processor 60 may determine whether there are further electrode combinations to test (106). For example, if programmer 14 stores a plurality of sense electrode combinations, processor 60 may record the bioelectrical brain signal sensed via each of the stored sense electrode combinations.

If there are additional sense electrode combinations with which to sense bioelectrical brain signals (106), processor 60 may determine the bioelectrical brain signal associated with each of the additional sense electrode combinations (100, 102, 104). If there are no additional sense electrode combinations available (106), processor 60 may map the sense electrode combinations to stimulation electrode combinations (108). That is, processor 60 may determine the stimulation electrode combinations that are associated with the sense electrode combinations. For example, processor 60 may reference a data structure that associates sense electrode combinations with stimulation electrode combinations in order to map the sense electrode combinations to stimulation electrode combinations. In other examples, processor 60 may initialize an algorithm to determine the stimulation electrode combinations that are associated with the sense electrode combinations if, for example, the sense electrode combinations are not pre-associated with stimulation electrode combinations.

Processor 60 may present the results to a user (109). As previously discussed, user interface 66 (FIG. 3) of programmer 14 may include a display, such as an LCD or LED display. Processor 60 may present the results of the sensing of bioelectrical brain signals via the different sense electrode combinations in any suitable manner. In some examples, processor 60 may display a time domain plot of the bioelectrical brain signal. In other examples, processor 60 may display a table that provides the relative beta band (or other frequency band of interest) power level associated with each sense electrode combination.

As previously described, in other examples, processor 40 of IMD 16 or another device may perform any part of the technique shown in FIG. 8. For example, processor 40 of IMD 16 may select a sense electrode combination from memory 42 (FIG. 3) of IMD 16 (100) and control sensing module 46 to sense a bioelectrical brain signal with the selected sense electrode combination (102). Processor 40 of IMD 16 may record the bioelectrical brain signal in memory 42, or transmit the signal to programmer 24 for recording in memory 62 (104). If there are additional sense electrode combinations with which to sense bioelectrical brain signals (106), processor 40 may determine the bioelectrical brain signal associated with each of the additional sense electrode combinations (100, 102, 104).

Processor 40 may uplink the results to programmer 24. The results may include, for example, the sense electrode combinations tested and the associated bioelectrical brain signals or specific signal characteristics (e.g., beta band power). Programmer 24 may then map the sense electrode combinations to stimulation electrode combinations (108) and present the results to a user (109). In other examples, processor 40 of IMD 16 may map the sense electrode combinations to stimulation electrode combinations (108).

Clinician interaction may be minimized if the technique shown in FIG. 8 for sensing bioelectrical brain signals with different sense electrode combinations is performed by processor 40 of IMD 16. This may help, for example, reduce the burden on the clinician during the stimulation electrode combination selection processor. While in some cases, the clinician may initialize the process, processor 40 of IMD 16 may control the selection of sense electrode combinations and recording of bioelectrical brain signals or other signal characteristics.

FIG. 9 is an example table that processor 60 may present to a user via a display of programmer 14 (108). A first column of the table shown in FIG. 9 indicates sense electrode combinations. While FIG. 9 indicates the sense electrode combinations via alphanumeric indicators (e.g., "Combination 1"), in other examples, processor 60 may present the sense electrode combinations to a user using other formats. In some examples, processor 60 may present a graphical display of leads 20 and indicate the subset of electrodes 24, 26 (FIG. 3) that are selected as part of each of the sense electrode combinations.

In some examples, the table shown in FIG. 9 may have selectable sections, such that a user may select one of the sections of the table in order to retrieve a subset of information associated with the selected section. For example, a user may select the box labeled, "COMBINATION 1" to receive more information about the first sense electrode combination in the table. The information may include, for example, the graphical display of the leads 20 and electrodes 24, 26 with an indication of the subset of electrodes 24, 26 that are included in the sense electrode combination associated with the indicator, "COMBINATION 1." In addition, programmer 14 may present information such as the stimulation electrode combination associated with the sense electrode combination, and, in some cases, other stimulation parameter values that map to or are otherwise related to the sense parameters.

The table shown in FIG. 9 also provides, for each of the sense electrode combinations, absolute beta band powers of the bioelectrical brain signal sensed via the respective sense electrode combination. These values are shown in the column with the headings "β POWER 1" and "β POWER 2." The beta band power levels of the bioelectrical brain signals may be calculating using different techniques. In some examples, the "β POWER 1" and "β POWER 2" columns shown in FIG. 9 may provide beta band power levels calculated using different techniques. For example, "β POWER 1" may indicate the average power in the beta band of the bioelectrical signal over a first time period, and "β POWER 2" column may indicate the average power in the beta band of the bioelectrical signal over a second time period that has a different duration than the first time period. As an example, the first time period may be about ten seconds and the second time period may be about one minute. Other time period durations are contemplated. The time periods may overlap or may not overlap.

In other examples, the "β POWER 1" and "β POWER 2" columns shown in FIG. 9 may provide beta band power levels calculated in different sub-bands of the beta band. For example, "β POWER 1" may indicate the average power in the 12 Hz sub-band of the beta band of the bioelectrical signal, and "β POWER 2" may indicate the average power in the 20 Hz sub-band of the beta band of the bioelectrical signal. The power levels in the different sub-bands of the beta band may be measured at the same or different times.

For each of the sense electrode combinations, the table shown in FIG. 9 may provide the relative beta band power level of the bioelectrical brain signal sensed via a respective one of the sense electrode combination. This is shown in the column with the heading "RELATIVE POWER." As previously indicated, the relative power may help reduce the variability in the different beta band power levels (shown in FIG. 9 under the heading "β Power 1") due to the differences in the overall power level of the sensed bioelectrical brain signals.

In some examples, processor 60 of programmer 14 may also label each sense electrode combination with a value or other indicator that indicates the possibility that a stimulation electrode combination associated with the sense electrode combination may provide efficacious therapy to patient 12. This label associated with each sense electrode combination may help a user compare the different sense electrode combinations relatively quickly and without undue effort. In the example shown in FIG. 9, indicators that processor 60 may present to a user to indicate the possibility that a stimulation electrode combination associated with the sense electrode combination may provide efficacious therapy to patient 12 includes an overall score and a confidence score for each sense electrode combination.

The overall score may include, for example, a weighted average of the beta band power levels in the "β POWER 1" and "β POWER 2" columns of the table shown in FIG. 9. Different weighting coefficients may be applied to the power levels in the "β POWER 1" and "β POWER 2" columns in order to calculate the overall score. The weighting coefficients may indicate, for example, the impact the power level in the "β POWER 1" or "β POWER 2" column has on the evaluation of a sense electrode combination. For example, if the value in the "β POWER 1" column indicates the average power in the 12 Hz sub-band of the beta band of the bioelectrical signal, and the value in the "β POWER 2" indicates the average power in the 20 Hz sub-band of the beta band of the bioelectrical signal, processor 60 of programmer 14 may determine that the 20 Hz sub-band of the beta band is more revealing of the patient's pathological brain state. Thus, processor 60 may apply a weighting coefficient to the value in the "β POWER 2" column to indicate that more weight should be applied to the "β POWER 2" value when calculating the average of the "β POWER 1" and "β POWER 2" values.

The confidence score may indicate, for example, how well the sense electrode combinations map to a stimulation electrode combination that provides efficacious stimulation therapy to patient 12. For example, processor 60 may store information in memory 62 (FIG. 4) that indicates that, based on previous patients or previous trials on patient 12, stimulation delivered with the electrodes of a particular stimulation electrode combination may not provide efficacious therapy to patient 12, even if the stimulation electrode combination is associated with a sense electrode combination that sensed a relatively high beta band power.

Processor 60 may also determine the confidence scores based on other information. In some examples, processor 60 may store information in memory 62 that indicates that for sense electrode combinations that sensed a bioelectrical brain signal comprising a relative beta band power levels at or above a particular threshold value, there is a relatively high probability that stimulation delivery via the stimulation electrode combination associated with the sense electrode combination may provide efficacious therapy to patient 12. A clinician, manually or with the aid of processor 60, may assign probabilities of efficacious stimulation to the different relative beta band power levels based on past experience with other patients. For example, based on observations for one or more patients, the clinician may record efficacy scores for each of a plurality of stimulation electrode combinations. The efficacy scores may be associated with different relative beta band power levels, which may be the relative beta band power level of a bioelectrical brain signal sensed with a sense electrode combination that is associated with the respective stimulation electrode combination.

An efficacy score may indicate the extent to which the patient's symptoms were mitigated and, in some cases, a rating of the severity of side effects from stimulation delivered via a particular stimulation electrode combination. The efficacy score may be based on subjective information, e.g., input from the patient, and/or may be based on physiological parameter measurements. A higher efficacy score may be associated with a higher probability that stimulation delivery via the stimulation electrode combination associated with the sense electrode combination may provide efficacious therapy to patient 12.

As an example of how the confidence score may be determined, if processor 60 determines that sense electrode "Combination 1" resulted in a relative beta band power level of 54, and a relative beta band power level at or above 50 is associated with an efficacy rating of 87% in memory 62, processor 60 determine that stimulation delivery via the stimulation electrode combination associated with sense electrode "Combination 1" may provide efficacious therapy to patient 12 at a confidence level of about 87%.

In other examples, processor 60 may present a power drain metric (not shown in FIG. 9) for each of the sense electrode combinations. The power drain metric may indicate the relative amount of power required to provide efficacious stimulation to patient 12 if stimulation is delivered to patient 12 via the stimulation electrode combination associated with the sense electrode combination. Some stimulation electrode combinations may include one electrode, defining a unipolar stimulation configuration, while other stimulation electrode combinations may include two or more electrodes, defining a bipolar stimulation configuration. The stimulation electrode combinations including fewer active electrodes may draw less current from stimulation generator 44 (FIG. 3), resulting in less power drain from power source 52 (FIG. 3) of IMD 16. The power drain metric may provide a numeric or other indication of the relative power drain based on factors such as the number of active electrodes in a stimulation electrode combination.

In some examples, the user may interact with programmer 14 to organize the sense electrode combinations by any one of the column headings. For example, the user may select "β POWER 1" column to organize the sense electrode combinations in ascending or descending order based on the absolute beta band powers. As another example, the user may determine the sense electrode combination that is associated with the highest overall score by selecting the "OVERALL SCORE" column. In examples in which user interface 66 (FIG. 4) of programmer 14 includes a touch screen display, the user may select a column of the table shown in FIG. 9 by selecting the box presented on the display. In other examples, the user may provide input using other input mechanisms, such as a keypad.

In some examples, a user may select a sense electrode combination from the list of combinations shown in FIG. 9 in order to further test the sense electrode combination and/or a stimulation electrode combination associated with the sense electrode combination. For example, the user may select a sense electrode combination by selecting the row of the table shown in FIG. 9 associated with the sense electrode combination or by manually inputting the sense electrode combination indicator via a keypad of programmer 14. Processor 60 of programmer 14 may receive the user input selecting the sense electrode combination and present a second display to the user that allows the user to input values for other stimulation parameters, such as stimulation amplitude, frequency, and pulse rate. Processor 60 may, for example, present a user interface including text boxes for receiving the values for the other stimulation parameters, pull-down menus that present preset values for the other stimulation parameter values, and the like.

Processor 60 may also provide a user interface that allows the user to indicate whether the stimulation electrode combination and other stimulation parameter values should be tested on patient 12. Upon receiving input from the user indicating a desire to test the stimulation electrode combination and other stimulation parameter values, processor 60 may provide a signal to processor 40 of IMD 16, which may control stimulation generator 44 (FIG. 3) to generate and deliver electrical stimulation to patient 12 via the stimulation electrode combination and the stimulation parameter values provided by the user.

Although a table is shown in FIG. 9, in other examples, processor 60 may present information to a user regarding the sense electrode combinations and the frequency characteristics of bioelectrical brain signals sensed via a respective one of the sense electrode combinations in any suitable format. In addition, processor 60 may present any type of information to a user via a display, such as the table shown in FIG. 9. For example, although not shown in FIG. 9, in some examples, a table presented to a user may include both sense electrode combinations and the associated stimulation electrode combinations.

In some examples, in addition to a frequency domain characteristic of a bioelectrical brain signal sensed via each of a plurality of sense electrode combinations, a stimulation electrode combination may be selected based on an impedance of an electrical path including the electrodes of the sense electrode combination that is mapped to the stimulation electrode combination. Thus, in some examples, the table shown in FIG. 9 may also display a complex impedance value or an electrical parameter value indicative of the complex impedance value (e.g., a voltage or current amplitude value) for each of the sense electrode combinations.

A complex impedance of an electrical path between electrodes of the sense electrode combination, and, therefore, through tissue of patient 12, may be measured using any suitable technique. In some examples, sensing module 46 (FIG. 3) of IMD 16 may include a chopper-stabilized superheterodyne amplifier shown in FIG. 14 of U.S. Patent Application Publication No. 2009/0082691 by Denison et al. The chopper-stabilized superheterodyne amplifier shown in FIG. 14 of U.S. Patent Application Publication No. 2009/0082691 by Denison et al. includes in-phase and quadrature signal paths with impedance measurement circuitry. The complex impedance may be measured during the same session in which the bioelectrical brain signals of brain 28 are sensed via the plurality of sense electrode combinations, e.g., a programming session.

The complex impedance measured via each of the sense electrode combinations may be useful for comparing the sense electrode combinations. The complex impedance measured via each sense electrode combination may be revealing of the location of the sense electrodes relative to the area of the patient's brain affected by the patient condition. In addition, the impedance measured via each of the sense electrode combinations may be indicative of the intensity of therapy that may be required to provide efficacious stimulation to patient 12 with the associated stimulation electrode combinations. The impedance may, for example, indicate the coupling efficiency between the electrodes of the sense electrode combination and the patient's tissue. For example, a relatively high impedance value may indicate that the coupling efficiency is lower, and, thus, a higher stimulation intensity is required in order to provide efficacious stimulation to patient 12 via a stimulation electrode combination associated with the sense electrode combination. On the other hand, a relatively low impedance value may indicate that the stimulation electrode combination associated with the sense electrode combination may be useful for providing efficacious therapy to patient 12 at a relatively low intensity, which may help conserve the power source 52 (FIG. 3) of IMD 16. Thus, in some examples, a clinician or a computing device (e.g., programmer 14) may compare the sense electrode combinations based on the frequency band characteristic and the complex impedance associated with each sense electrode combination.

After a sense electrode combination is selected, e.g., using the technique shown in FIG. 5, processor 40 of IMD 16 may control stimulation generator 44 (FIG. 3) to generate and deliver electrical stimulation therapy to patient 12 on a chronic basis. Leads 20 may move within patient 12 over time, or the patient's disease state may change, such that stimulation delivery via the selected stimulation electrode combination may no longer provide the most efficacious therapy to patient 12. In some examples, after the selection of a stimulation electrode combination, processor 40 of IMD 16 may periodically evaluate the stimulation electrode combination to determine whether another stimulation electrode combination may provide more efficacious therapy to patient 12. FIG. 10 is a flow diagram of an example technique that processor 40 may implement in order to evaluate a currently-selected stimulation electrode combination (referred to as a "first stimulation electrode combination" in the flow diagram shown in FIG. 10). In other examples, processor 60 of programmer 14 or another device may perform any part of the technique shown in FIG. 10.

Processor 40 may control switch module 48 (FIG. 3) and stimulation generator 44 (FIG. 3) to deliver electrical stimulation to patient 12 with a first stimulation electrode combination (110). Processor 40 may control sensing module 46 and switch module 48 to sense a bioelectrical brain signal with a first sense electrode combination that is associated with the first stimulation electrode combination (112). This bioelectrical brain signal may include, for example, a local field potential within brain 28. Processor 40 determines a first relative beta band power level of the first bioelectrical brain signal (114), e.g., using the techniques described above with reference to FIG. 5.

Processor 40 may also evaluate one or more other sense electrode combinations in order to determine whether stimulation delivery via the first stimulation electrode combination is relatively efficacious. In the example shown in FIG. 10, processor 40 may select a second sense electrode combination from memory 42, and sense a second bioelectrical brain signal via the second sense electrode combination (116). The second sense electrode combination may be associated with a different stimulation electrode combination than the first sense electrode combination. Processor 40 determines a second relative beta band power level of the second bioelectrical brain signal (118), e.g., using the techniques described above with reference to FIG. 5.

In the example shown in FIG. 10, processor 40 compares the first and second relative beta band power levels (120). If processor 40 determines that the first relative beta band power level is greater than or equal to the second relative beta band power level (120), processor 40 may determine that stimulation delivery via the first stimulation electrode combination is either more efficacious or provides at least the same degree of efficacy as stimulation delivery via the second stimulation electrode combination. If the first relative beta band power is greater than the second relative beta band power level, processor 40 may determine that the first stimulation electrode combination provides stimulation therapy to a more relevant target tissue site within brain 28 than the second stimulation electrode combination. Thus, processor 40 may continue controlling switch module 48 and stimulation generator 44 to deliver electrical stimulation to patient 12 with the first stimulation electrode combination (110).

If processor 40 determines that the first relative beta band power level is not greater than or equal to the second relative beta band power level (122), processor 40 may determine that the second stimulation electrode combination provides stimulation therapy to a more relevant target tissue site within brain 28 than the first stimulation electrode combination. Thus, processor 40 may deliver stimulation to brain 28 with the second stimulation electrode combination associated with the second sense electrode combination (122). In other examples, processor 40 may sense bioelectrical brain signals with additional sense electrode combinations in order to determine whether stimulation delivery with the second stimulation electrode combination provides relatively efficacious therapy.

In some examples, processor 40 may also measure the impedance of the electrical paths through tissue via each of the sense electrode combinations in order to further evaluate the stimulation electrode combinations, as described above with respect to FIG. 9. For example, upon determining that the impedance measured via the first sense electrode combination associated with the first stimulation electrode combination has increased by a threshold amount, processor 40 may begin evaluating other stored sense electrode combinations to determine whether another stimulation electrode combination may provide more efficacious therapy to patient 12, e.g., with lower power consumption.

Various examples of the disclosure have been described. These and other examples are within the scope of the following example claims.

What is claimed is:

1. A method comprising:
   receiving, by a processor of a therapy system, a plurality of bioelectrical signals, wherein each of the bioelectrical signals is sensed within a patient by a sensing module with a respective sense electrode combination of a plurality of sense electrode combinations, each of the sense electrode combinations being associated with a respective one of a plurality of stimulation electrode combinations;
   for each of the sense electrode combinations, generating, by the processor, an indicator based on the bioelectrical signal sensed with the respective sense electrode combination, wherein the indicator indicates a possibility that electrical stimulation delivered by a medical device with the stimulation electrode combination associated with the sense electrode combination will provide efficacious therapy to the patient, and wherein generating the indicator comprises comparing a characteristic of the bioelectrical signal sensed with the respective sense electrode combination with stored information; and
   presenting, via a display, indications of the sense electrode combinations and the respective indicators.

2. The method of claim 1, wherein generating the indicator comprises generating, for each of the sense electrode combinations, the indicator based on a frequency domain characteristic of the bioelectrical signal sensed with the respective sense electrode combination.

3. The method of claim 2, wherein generating the indicator comprises generating the indictor based on a weighted average of beta band power levels of the bioelectrical signal sensed with the respective sense electrode combination.

4. The method of claim 2, wherein generating the indicator based on the frequency domain characteristic comprises:
   determining the frequency domain characteristic of the bioelectrical signal sensed with the respective sense electrode combination; and
   comparing the frequency domain characteristic to stored information, wherein the stored information is based on at least one of bioelectrical signals sensed within other patients or bioelectrical signals previously sensed within the patient.

5. The method of claim 1, wherein the stored information indicates, for each stored bioelectrical brain signal of a plurality of stored bioelectrical brain signals, an outcome of electrical stimulation therapy delivered via a stimulation electrode combination associated with the stored bioelectrical brain signal.

6. The method of claim 1, wherein generating the indicator comprises generating a confidence score that indicates whether the stimulation electrode combination associated with the sense electrode combination will provide efficacious stimulation therapy to the patient.

7. The method of claim 6, wherein generating the confidence score comprises comparing the characteristic of the bioelectrical signal with the stored information, the stored information indicating at least one of efficacious or inefficacious stimulation electrode combinations determined based on testing of the stimulation electrode combinations on a group of patients.

8. The method of claim 6, wherein generating the confidence score comprises comparing the characteristic of the bioelectrical signal with the stored information, the stored information indicating at least one of efficacious or inefficacious stimulation electrode combinations for the patient, and the stored information being based on previous testing of the stimulation electrode combinations on the patient.

9. The method of claim 6, wherein generating the confidence score comprises comparing the characteristic of the bioelectrical signal with the stored information, the stored information associating a probability of efficacious stimulation with the respective sense electrode combination.

10. The method of claim 9, wherein the probability of efficacious stimulation is based on historical data from one or more other patients.

11. The method of claim 9, wherein the probability of efficacious stimulation is based on a frequency domain characteristic of the bioelectrical brain signal sensed with the respective sense electrode combination.

12. The method of claim 9, wherein the stored information associates a relatively high probability of efficacious stimulation with the stimulation electrode combination associated with a sense electrode combination with which a bioelectrical brain signal exhibiting a relative beta band power level at or above a threshold value was sensed.

13. The method of claim 9, further comprising generating the probability of efficacious stimulation for a sense electrode combination, wherein generating the probability of efficacious stimulation comprises:
   determining the frequency domain characteristic of a bioelectrical brain signal sensed via the sense electrode combination;

determining an efficacy score associated with the frequency domain characteristic in a memory; and
generating the probability of efficacious stimulation based on the efficacy score.

14. The method of claim 13, wherein the efficacy score indicates at least one of an extent to which symptoms are mitigated or a rating of the severity of side effects from electrical stimulation delivered via the stimulation electrode combination associated with the sense electrode combination.

15. The method of claim 1, further comprising selecting, by the processor, at least one of the stimulation electrode combinations based on the generated indicators.

16. The method of claim 15, further comprising controlling the medical device to deliver electrical stimulation to the patient via the at least one of the stimulation electrode combinations selected based on the generated indicators.

17. The method of claim 1, wherein at least one of the sense electrode combinations includes at least one of a partial ring electrode or a segmented electrode.

18. The method of claim 1, wherein at least one of the sense electrode combinations includes a ring electrode.

19. A system comprising:
a memory; and
a processor configured to receive a plurality of bioelectrical signals, wherein each of the bioelectrical signals is sensed within a patient by a sensing module with a respective sense electrode combination of a plurality of sense electrode combinations, each of the sense electrode combinations being associated with a respective one of a plurality of stimulation electrode combinations, and, for each of the sense electrode combinations, generate an indicator based on the bioelectrical signal sensed with the respective sense electrode combination, wherein the indicator indicates a possibility that electrical stimulation delivered by a medical device with the stimulation electrode combination associated with the sense electrode combination will provide efficacious therapy to the patient, wherein the processor is configured to store the indicators in the memory, and wherein the processor is configured to generate the indicator by at least comparing a characteristic of the bioelectrical signal sensed with the respective sense electrode combination with information stored by the memory.

20. The system of claim 19, further comprising a display, wherein the processor is configured to present, via the display, a list of the sense electrode combinations and the respective indicators.

21. The system of claim 19, wherein the processor is configured to generate the indicator based on a frequency domain characteristic of the bioelectrical signal sensed with the respective sense electrode combination.

22. The system of claim 21, wherein the frequency domain characteristic comprises a weighted average of beta band power levels of the bioelectrical signal sensed with the respective sense electrode combination.

23. The system of claim 21, wherein the processor is configured to generate the indicator by at least determining the frequency domain characteristic of the bioelectrical signal sensed with the respective sense electrode combination, and comparing the frequency domain characteristic to the information stored by the memory, wherein the information is based on at least one of bioelectrical signals sensed within other patients or bioelectrical signals previously sensed within the patient.

24. The system of claim 19, wherein the information stored by the memory indicates, for each stored bioelectrical brain signal of a plurality of stored bioelectrical brain signals, an outcome of electrical stimulation therapy delivered via a stimulation electrode combination associated with the stored bioelectrical brain signal.

25. The system of claim 19, wherein the processor is configured to generate the indicator by at least generating, for each of the sense electrode combinations, a confidence score that indicates whether the stimulation electrode combination associated with the respective sense electrode combination will provide efficacious stimulation therapy to the patient.

26. The system of claim 25, wherein the processor is configured to generate the confidence score by at least comparing the characteristic of the bioelectrical signal sensed with the respective sense electrode combination with the information stored by the memory, the information indicating at least one of efficacious or inefficacious stimulation electrode combinations determined based on testing of the stimulation electrode combinations on a group of patients.

27. The system of claim 25, wherein the processor is configured to generate the confidence score by at least comparing the characteristic of the bioelectrical signal sensed with the respective sense electrode combination with the information stored by the memory, the information associating a probability of efficacious stimulation with the sense electrode combination.

28. The system of claim 27, wherein the probability of efficacious stimulation is based on historical data from one or more other patients.

29. The system of claim 27, wherein the probability of efficacious stimulation is based on a frequency domain characteristic of the bioelectrical brain signal sensed with the respective sense electrode combination.

30. The system of claim 27, wherein the information associates a relatively high probability of efficacious stimulation with the stimulation electrode combination associated with a sense electrode combination with which a bioelectrical brain signal exhibiting a relative beta band power level at or above a threshold value was sensed.

31. The system of claim 27, wherein the processor is further configured to generate the probability of efficacious stimulation for a sense electrode combination by at least:
determining the frequency domain characteristic of the bioelectrical brain signal sensed via the sense electrode combination;
determining an efficacy score associated with the frequency domain characteristic in a memory; and
generating the probability of efficacious stimulation based on the efficacy score.

32. The system of claim 31, wherein the efficacy score indicates at least one of an extent to which symptoms are mitigated or a rating of the severity of side effects from electrical stimulation delivered via the stimulation electrode combination associated with the sense electrode combination.

33. The system of claim 25, wherein the processor is configured to generate the confidence score by at least comparing the characteristic of the bioelectrical signal sensed with the respective sense electrode combination with the information stored by the memory, the information indicating at least one of efficacious or inefficacious stimulation electrode combinations for the patient, and the information being based on previous testing of the stimulation electrode combinations on the patient.

34. The system of claim 19, wherein the processor is further configured to select at least one of the stimulation electrode combinations based on the generated indicators.

35. The system of claim 34, further comprising the medical device, wherein the processor is configured to control the medical device to deliver electrical stimulation to the patient via the at least one of the stimulation electrode combinations selected based on the generated indicators.

36. The system of claim 19, wherein at least one of the sense electrode combinations includes at least one of a partial ring electrode or a segmented electrode.

37. The system of claim 19, wherein at least one of the sense electrode combinations includes a ring electrode.

38. A system comprising:
means for receiving a plurality of bioelectrical signals, wherein each of the bioelectrical signals is sensed within a patient by a sensing module with a respective sense electrode combination of a plurality of sense electrode combinations, each of the sense electrode combinations being associated with a respective one of a plurality of stimulation electrode combinations; and
means for generating, for each of the sense electrode combinations, an indicator based on the bioelectrical signal sensed with the respective sense electrode combination by at least comparing a characteristic of the bioelectrical signal sensed with the respective sense electrode combination with stored information, wherein the indicator indicates a possibility that electrical stimulation delivered by a medical device with the stimulation electrode combination associated with the sense electrode combination will provide efficacious therapy to the patient.

39. The system of claim 38, wherein the means for generating the indicator generates the indicator by at least determining a frequency domain characteristic of the bioelectrical signal sensed with the respective sense electrode combination and comparing the frequency domain characteristic to stored information, wherein the stored information is based on at least one of bioelectrical signals sensed within other patients or bioelectrical signals previously sensed within the patient.

40. A non-transitory computer-readable medium comprising instructions that, when executed by a processor, cause the processor to:
receive a plurality of bioelectrical signals, wherein each of the bioelectrical signals is sensed within a patient by a sensing module with a respective sense electrode combination of a plurality of sense electrode combinations, each of the sense electrode combinations being associated with a respective one of a plurality of stimulation electrode combinations; and
for each of the sense electrode combinations, generate an indicator based on the bioelectrical signal sensed with the respective sense electrode combination by at least comparing a characteristic of the bioelectrical signal with stored information, wherein the indicator indicates a possibility that electrical stimulation delivered by a medical device with the stimulation electrode combination associated with the sense electrode combination will provide efficacious therapy to the patient.

41. The computer-readable medium of claim 40, further comprising instructions that, when executed by the processor, cause the processor to generate the indicator by at least:
determining a frequency domain characteristic of the bioelectrical signal sensed with the respective sense electrode combination; and
comparing the frequency domain characteristic to stored information, wherein the stored information is based on at least one of bioelectrical signals sensed within other patients or bioelectrical signals previously sensed within the patient.

\* \* \* \* \*